US005945307A

United States Patent [19]
Glucksmann et al.

[11] Patent Number: 5,945,307
[45] Date of Patent: Aug. 31, 1999

[54] ISOLATED NUCLEIC ACID MOLECULES ENCODING A G-PROTEIN COUPLED RECEPTOR SHOWING HOMOLOGY TO THE 5HT FAMILY OF RECEPTORS

[75] Inventors: M. Alexandra Glucksmann, Lexington; Keith Robison, Wilmington, both of Mass.

[73] Assignee: Millennium Pharmaceuticals, Inc., Cambridge, Mass.

[21] Appl. No.: 09/013,634

[22] Filed: Jan. 26, 1998

[51] Int. Cl.[6] .......................... C12N 15/12; C07K 14/705
[52] U.S. Cl. .................... 435/69.1; 536/23.5; 435/252.3; 435/254.11; 435/320.1; 435/325
[58] Field of Search ......................... 536/23.5; 435/69.1, 435/320.1, 325, 352.3, 254.11

[56] References Cited

PUBLICATIONS

Adams, M.D. et al., "Rapid cDNA Sequencing (Expressed Sequence Tags) from a Directionally Clones Human Infant Brain cDNA Library," *Nature Genet.*, vol. 4, 373–80 (1993).
Allard W.J. et al., "Sequence of the Gene Encoding the Human M1 Muscarinic Acetylcholine Receptor," *Nucleic Acids Res.*, vol. 15, No. 24, 10604 (1987).
Arden, J.R. et al., "Mutational Analysis of Third Cytoplasmic Loop Domains in G–protein Coupling of the HM1 Muscarinic Receptor," *Biochem. Biophys. Res. Commun.*, vol. 188, No. 3, 1111–5 (1992).
Bonner, T.I. et al., "Cloning and Expression of the Human and Rat m5 Muscarinic Acetylcholine Receptor Genes," *Neuron*, vol. 1, No. 5, 403–10 (1988).
Bonner, T.I. et al., "Identification of a Family of Muscarinic Acetylcholine Receptor Genes," *Science*, vol. 237, No. 4814, 527–32 (1987).
Braun, T. et al., "A Novel Subtype of Muscarinic Receptor Identified by Homology Screening," *Biochem. Biophys. Res. Commun.*, vol. 149, No. 1, 125–32 (1987).
Chapman, C.G. and Browne, M.J., "Isolation of the Human m1 (Hm1) Muscarinic Acetylcholine Receptor Gene by PCR Amplification," *Nucleic Acids Res.*, vol. 18, No. 8, 2191 (1990).
Erlander, M.G. et al., "Two Members of a Distinct Subfamily of 5–Hydroxytryptamine Receptors Differentially Expressed in Rat Brain," *PNAS*, vol. 90, No. 8, 3452–6 (1993).
Kubo, T. et al., "Cloning, Sequencing and Expression of Complementary DNA Encoding the Muscarinic Acetylcholine Receptor," *Nature*, vol. 323, No. 6087, 411–6 (1986).
Lei, J. et al., "The Molecular Properties of the M1 Muscarinic Receptor and its Regulation of Cytosolic Calcium in a Eukaryotic Gene Expression System," *Adv. Exp. Med. Biol.*, vol. 287, 313–30 (1991).
Lamers, A.E. et al., "Cloning and Sequence Analysis of a Hypothalamic cDNA Encoding a D1c Dopamine Receptor in Tilapia," *Biochim. Biophys. Acta*, vol. 1308, No. 1, 17–22 (1996).

Lee, P.H. et al., "Cloning and Expression of a cDNA Encoding Bovine Muscarinic Acetylcholine m3 Receptor," *Biochim. Biophys. Acta*, vol. 1223, No. 1, 151–4 (1994).
Matthes, H. et al., "Mouse 5–hydroxytryptamine5A and 5–hydroxytryptamine5B Receptors Define a New Family of Serotonin Receptors: Cloning, Functional Expression, and Chromosomal Localization," *Mol. Pharmacol.*, vol. 43, No. 3, 313–9 (1993).
Orange, P.R. et al., "Allelic Variations of the Human Histamine H2 Receptor Gene," *Neuroreport*, vol. 7, 1293–6 (1996).
Peralta, E.G. et al., "Distinct Primary Structures, Ligand–binding Properties and Tissue–specific Expression of Four Human Muscarinic Acetylcholine Receptors," *EMBO J.*, vol. 6, No. 13, 3923–9 (1987).
Probst, W. et al., "Sequence Alignment of the G–Protein Coupled Receptor Superfamily," *DNA and Cell Biology*, vol. 11, No. 1, 1–20 (1992).
Rees, S. et al., "Cloning and Characterization of the Human 5–HT5A Serotonin Receptor," *FEBS Lett.*, vol. 355, No. 3, 242–6 (1994).
Sadou, F. and Hen, R., "5–Hydroxytryptamine Rceptor Subtypes in Vertebrates and Invertebrates," *Neurochem. Int.*, vol. 25, No. 6, 503–32 (1994).
Savarese, T.M. et al., "Site–directed Mutagenesis of the Rat m1 Muscarinic Acetylcholine Receptor. Role of Conserved Cysteines in Receptor Function," *J. Biol. Chem.*, vol. 267, No. 16, 11439–48 (1992).
Shen, B. et al., "Partial Sequencing and Mapping of Clones from Two Maize cDNA Libraries," *Plant Mol. Biol.*, vol. 26, 1085–1101 (1994).
Wess, J. et al., "Role of Conserved Threonine and Tyrosine Residues in Acetylcholine Binding and Muscarinic Receptor Activation," *The Journal of Biological Chemistry*, vol. 267, No. 27, 19313–9 (1992).
Wess, J. et al., "Site–directed Mutagenesis of the m3 Muscarinic Receptor: Identification of a Series of Threonine and Tyrosine Residues Involved in Agonist but not Antagonist Binding," *EMBO J.*vol. 10, No. 12, 3729–34 (1991).
Wisden, W. et al., "Cloning and Characterization of the Rat 5–HT5B Receptor. Evidence that the 5–HT5B Receptor Couples to a G Protein in Mammalian Cell Membranes," *FEBS Lett.*, vol. 333, Nos. 1–2, 25–31 (1993).
Witz, P. et al., "Cloning and Characterization of a Drosophila Serotonin Receptor that Activates Adenylate Cyclase," *PNAS*, vol. 87, No. 22, 8940–4 (1990).
Yamashita, M. et al., "Expression Cloning of a cDNA Encoding the Bovine Histamine H1 Receptor," *PNAS*, vol. 88, No. 24, 11515–9 (1991).

*Primary Examiner*—Sally P. Teng
*Attorney, Agent, or Firm*—Lahive & Cockfield, LLP; Amy E. Mandragouras

[57] ABSTRACT

The present invention provides isolated nucleic acid molecules encoding a G-protein coupled receptor that shows homology to the 5HT family of receptors. The present invention further provides vectors containing the nucleic acid molecules, hosts transformed or transfected with the nucleic acid molecules and methods of producing the G-protein coupled receptor.

16 Claims, 5 Drawing Sheets

FIG. 1A

CGACCCACGCGTCCGGGGAGGCCCTGAGGCTCCGGGTGCCGCCGCCCTCTGGAGC
CATGGGGCTGGGGCCG
GGGGTCGCCGGCGGCGGGGGCCGAGGGGTGAGCCGGCCGCGGGCAGCGCCATGGCGGC
GCCGGGTGCGACCCTG
AGCGCCGGCGGGGGCGCACCATGAACTCGTGGACGCGGGGCTGGCGGGGCTACTGGTG
GGCACGATGGGGTCTCG
CTGCTGTCCAACGCGCTGGTGCTCTGCTGCTGCACAGCGGACATCCGCCGCCAGGCG
CCGGCGCTCTTCACCCT
GAACCTCACGTGCGGGAACCTGCTCAACATGCCCTCACGCTGGCCGCCGT
CGTGGGCGGGGCAGC
CGGCGGGACCGCCTGTGCCGCCTGGCTGCCCTTCCTCGACACCTTCCTGGCTGCCAACTCCAT
GCTCAGCATGGCCGCG
CTCAGCATCGACCGCTGGGTGGCCGTGTCTTCCCGCTGAGCTACCGGCCAAGATGCGCTC
CGCGACGCGGCGCTCAT
GGTGCCTACACGTGGCTGCACGCCGAGCGCCCTCACCTTCCCAGCCGCCCTGTCCTGGCTC
GGCTTCCACCAGCTGT
ACGCCCTCGTGCAGGCTGCACGCTGTGCAGCGCTACCTCAAGGTGTCAAGGTGGCCCGCT
GCGCCTTCCACGCTCTC
AGCTTCCTGCTCTTCCTGTGCTCTGCTGCACGTACCTCAAGGTGTCAAGGTGGCCCGCT
TCCATTGCAAGCGCAT
CGACGTGATCACCATGCAGAGCTCGATGAGAAGATCAGCACCTTCATAGGACCTTCCTTGTGTGCT
CTGTCTGGAGGAGCAGA
AGCGGAGGCGACAGCAGCGACGAGCCACCAAGAAGATCAGCACCTTCATAGGACCTTCCTTGTGTGCT
TCGCGCCTATGTGATC
ACCAGGCTAGTGAGCTCTTCTCCACGGTGCCCATGCGGCTCCCACTGGCTCGTGTCCAAG
TGCTTGGCGTACAGCAA
GGCCGCATCCGACCCCTTGTGTACTCCTTACTGCGACACCAGTACCGCAAAAGTCGAAGA
GATTCTGAACAGGCTCC

FIG. 1B

TGCACAGACGCTCCATCCACTCCTCTGGCCTCACAGGGGACTCTCACAGCCAGAACATTCTGCC
GGTGTCTGAGTGAAGG
ACCGCGCTCCTGCTGAAGAGTTTAGAATGAGGCAGCGGGTGAGAAGAAGGGTGGGAGGGCGTG
GGGGCCCCTGGGTGGACA
CCACCAGCCACCAGTCCCTGGCATGCCCAGATGATCCTGGTTCCCTGGCTTGTAGGGCTCCA
GAGCCTGCTTCCCTGGTT
CCTCAAGGGCAGATATTGGACACTTCCTTATTGTCACCAAAGGAATGACTGTAGGCCGTGTG
TTGGCCCTTCTTTCTAA
GAAGCTGCTTTGAGCTCCTGACTCACCTGAGGCTCCCTGGGGATGACACTCAGTTCTGTCA
CTGTCAAGGATGCAGAG
AGCTGGTGGTAGGTGGGAAGCATGTGTCCACCTGCTGTCGACGCTGCTCCATG
CTGAAGAAAGTGACAG
TCTCCAGGGACATTTCAGCCATGCTGAAGGAGGCTGGCAGTGTCATTGGCCGGATCTA
ACATGCCACCTGCTCTC
CACAGGGTAGGTGGTGCCTTCAACCCAAATATTATTCAGCTGGTACTAACGACATTGTGCC
CAGCTGGGACTCTTGGG
CTCTGTGCCAGGGAAAATGTTTCACAACTAGTGGCTGCCAATTGCTGCTGACCAGTTGTCT
TAGAAATGGTCAATG
GATTCAACTTTAGTCCCTCCCCTAAAAGCGAATGTTTGTGTGCAGACAATCTTAGC
ATGAAAATGGTTTAAA
TAGGCTGGTCCTACATGTATTAGGTTCTTTCAAGTTTGACTGGGAGGTCACCTTTTCTGATTT
ACAAGTCCTAATTGTT
GGAGCTCAGTAAAGGTAGGAGGAAGGTGGCTGGTTGGTCCCTTCCCCTGTTGTGACCT
GAATTTACAGGAAGTGT
TTCAACTTGTCTTATGCATCTTATCTGGCATGTCCTGGGAGATGGATGGGCAAGAACTGGCCT
GAGCAGGGATTTTTTGCC

FIG.1C

TTGATTTTAAGTCACTGGGTTCCATTGTCCTGGCACCTCCATTTCCTTAGTTTCTGTAAGCCTGT
TAACAGAAAGTAGAG
GCTATTCAAGGTTATCAAGAAAGTGCCCTGTGCTAATGATGAGACAGTGAATTTTTTTTTTTTT
CAGATGGGAGTTTCAC
TCTTATTGCCCAGGCTAGAGTGCAATGTGCGATCTAGGCTCACCGCAACCTCTGCCTTCCAGG
TTCAAGTGATTAGAGA
CAGTGAAATTTTTATGGAATACTGCACCTATAAACACATGCCAATCTGTTAGCAGTCCTGACT
TGATTTAATAAAACC
AAGGAGAGCCAAAAAAAAAAAAAAAAAAAAAAAAAAAAAAGGGCCGCTCTAGAGGATCC
AAGCTTACGTACGGTGCA
TGCCGACGTCATAGCTCTTGGA

FIG. 2

ATGAACTCGTGGACGCGGGCCTGCCGGGGCTACTGGTGGGCACGATGGGCGTCTCGCTGTCCAACGCGCTGGTGCT

GCTCTGCCTGCTGCACAGCGCGGACATCCGCGCCAGGCGCCGGCGCTCTTCACCCTGAACCTCACGTGCGGGAACCTGC

TGTGCACCGTGGTCAACATGCCGCTCACGCGCTGGCCGGCGTGTGCGGCAGCCGGGGGACCGCCTGTGCCGC

CTGGCTGCCCTTCCTCGACACCTTCCTGGCTGCCAACTCCATGCTCAGCATGCCGCGCTCAGCATGGACCGCTGGGTGGC

CGTGGTCTTCCCGCTGAGCTACCGGGCCAAGATGCGCCTCCGCGACGCGGGCGCTCATGGTGGCCTACACGTGGCTGCACG

CGCTCACCTTCCCAGCCGCTCGCGCCGTCCTGGCTTCCACCAGCTGTACGCCTCGTGCACGCTGTGCAGC

CGGCGGCCGGACGAGCGCCTGCTTCGCCTGCTTCACTGGCGCTCCACGCTTCCTGCTCTCCTTCGTCGT

GCTCTGCTGCACGTACTTCAAGGTGCTGCACCCCAGTGTGCGGGAACGCTGTCTGGAGGAGCAGAAGCGGAGCGAGCCACC

TCGTGCTGCTGGTGGACCTGCACCTTCCTTCATAGGACCTTGTGTGCTTCGCGCCCTATGTGATCACCAGCTAGTGGAGCTCTTCTC

AAGAAGATCAGCACCTTCATAGGACCTTGTGTGCTTCGCGCCCTATGTGATCACCAGCTAGTGGAGCTCTTCTC

CACGGTGCCCATCGGCTCCCACTGTGGGGTGCTGTCCAAGTGCTTGGCGTACAGCAAGGCCGCATCCGACCCCTTTGTGT

ACTCCTTACTGCGACACCAGTACCGCCAAAAGCTGCAAGGAGATTCTGAACAGGCTCCTGCACAGACGCTCCATCCACTCC

TCTGGCCCTCACAGGCGACTCTCACAGCCAGAACATTCTGCCGGTGTCTGAGTGA

FIG. 3

MNSWDAGLAGLLVGTMGVSLLSNALVLLCLLHSADIRRQAPALFTLNLTCGNLLCTVVNMPLTTLAGVVARRQPAGDRLCR

LAAFLDTFLAANSMLSMAALSIDRWVAVVFPLSYRAKMRLRDAALMVAYTWLHALTFPAAALALSWLGFHQLYASCTLCS

RRPDERLRFAVFTGAFHALSFLLSFVVLCCTYLKVLKVARFHCKRIDVITMQTLVLLVDLHPSVRERCLEEQKRRQRAT

KKISTFIGTFLVCFAPYVITRLVELFSTVPIGSHWGVLSKCLAYSKAASDPFVYSLLRHQYRKSCKEILNRLLHRRSIHS

SGLTGDSHSQNILPVSE

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 2581 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 184..1194

(xi) SEQUENCE DESCRIPTION: SEQ ID NO:1:

```
CGACCCACGC GTCCGCGGGA GGCCGCCTGA GGCTCCGGGG TGGCCGCGCG CCCTCCTGGG        60

AGCCATGGCG GCTGGGGCCG GGGGTCGCCG GGCGGCGGCG GCGCCGAGGG GCTGAGCCGG       120

CCGCGGGCAG CGCCATGGCG GCGCCGGGTT GCGGACCCTG AGCGCCGGCG CGGGGCGCGC       180

ACC ATG AAC TCG TGG GAC GCG GGC CTG GCG GGG CTA CTG GTG GGC ACG        228
    Met Asn Ser Trp Asp Ala Gly Leu Ala Gly Leu Leu Val Gly Thr
    1               5                   10                  15

ATG GGC GTC TCG CTG CTG TCC AAC GCG CTG GTG CTG CTC TGC CTG CTG        276
Met Gly Val Ser Leu Leu Ser Asn Ala Leu Val Leu Leu Cys Leu Leu
                20                  25                  30

CAC AGC GCG GAC ATC CGC CGC CAG GCG CCG GCG CTC TTC ACC CTG AAC        324
His Ser Ala Asp Ile Arg Arg Gln Ala Pro Ala Leu Phe Thr Leu Asn
            35                  40                  45

CTC ACG TGC GGG AAC CTG CTG TGC ACC GTG GTC AAC ATG CCG CTC ACG        372
Leu Thr Cys Gly Asn Leu Leu Cys Thr Val Val Asn Met Pro Leu Thr
        50                  55                  60

CTG GCC GGC GTC GTG GCG CGG CGG CAG CCG GCG GGC GAC CGC CTG TGC        420
Leu Ala Gly Val Val Ala Arg Arg Gln Pro Ala Gly Asp Arg Leu Cys
    65                  70                  75

CGC CTG GCT GCC TTC CTC GAC ACC TTC CTG GCT GCC AAC TCC ATG CTC        468
Arg Leu Ala Ala Phe Leu Asp Thr Phe Leu Ala Ala Asn Ser Met Leu
80                  85                  90                  95
```

```
AGC ATG GCC GCG CTC AGC ATC GAC CGC TGG GTG GCC GTG GTC TTC CCG         516
Ser Met Ala Ala Leu Ser Ile Asp Arg Trp Val Ala Val Val Phe Pro
        100                 105                 110

CTG AGC TAC CGG GCC AAG ATG CGC CTC CGC GAC GCG GCG CTC ATG GTG         564
Leu Ser Tyr Arg Ala Lys Met Arg Leu Arg Asp Ala Ala Leu Met Val
        115                 120                 125

GCC TAC ACG TGG CTG CAC GCG CTC ACC TTC CCA GCC GCC GCG CTC GCC         612
Ala Tyr Thr Trp Leu His Ala Leu Thr Phe Pro Ala Ala Ala Leu Ala
        130                 135                 140

CTG TCC TGG CTC GGC TTC CAC CAG CTG TAC GCC TCG TGC ACG CTG TGC         660
Leu Ser Trp Leu Gly Phe His Gln Leu Tyr Ala Ser Cys Thr Leu Cys
    145                 150                 155

AGC CGG CGG CCG GAC GAG CGC CTG CGC TTC GCC GTC TTC ACT GGC GCC         708
Ser Arg Arg Pro Asp Glu Arg Leu Arg Phe Ala Val Phe Thr Gly Ala
160                 165                 170                 175

TTC CAC GCT CTC AGC TTC CTG CTC TCC TTC GTC GTG CTC TGC TGC ACG         756
Phe His Ala Leu Ser Phe Leu Leu Ser Phe Val Val Leu Cys Cys Thr
                180                 185                 190

TAC CTC AAG GTG CTC AAG GTG GCC CGC TTC CAT TGC AAG CGC ATC GAC         804
Tyr Leu Lys Val Leu Lys Val Ala Arg Phe His Cys Lys Arg Ile Asp
        195                 200                 205

GTG ATC ACC ATG CAG ACG CTC GTG CTG CTG GTG GAC CTG CAC CCC AGT         852
Val Ile Thr Met Gln Thr Leu Val Leu Leu Val Asp Leu His Pro Ser
        210                 215                 220

GTG CGG GAA CGC TGT CTG GAG GAG CAG AAG CGG AGG CGA CAG CGA GCC         900
Val Arg Glu Arg Cys Leu Glu Glu Gln Lys Arg Arg Arg Gln Arg Ala
    225                 230                 235

ACC AAG AAG ATC AGC ACC TTC ATA GGG ACC TTC CTT GTG TGC TTC GCG         948
Thr Lys Lys Ile Ser Thr Phe Ile Gly Thr Phe Leu Val Cys Phe Ala
240                 245                 250                 255

CCC TAT GTG ATC ACC AGG CTA GTG GAG CTC TTC TCC ACG GTG CCC ATC         996
Pro Tyr Val Ile Thr Arg Leu Val Glu Leu Phe Ser Thr Val Pro Ile
                260                 265                 270

GGC TCC CAC TGG GGG GTG CTG TCC AAG TGC TTG GCG TAC AGC AAG GCC        1044
Gly Ser His Trp Gly Val Leu Ser Lys Cys Leu Ala Tyr Ser Lys Ala
        275                 280                 285

GCA TCC GAC CCC TTT GTG TAC TCC TTA CTG CGA CAC CAG TAC CGC AAA        1092
Ala Ser Asp Pro Phe Val Tyr Ser Leu Leu Arg His Gln Tyr Arg Lys
        290                 295                 300

AGC TGC AAG GAG ATT CTG AAC AGG CTC CTG CAC AGA CGC TCC ATC CAC        1140
Ser Cys Lys Glu Ile Leu Asn Arg Leu Leu His Arg Arg Ser Ile His
    305                 310                 315

TCC TCT GGC CTC ACA GGC GAC TCT CAC AGC CAG AAC ATT CTG CCG GTG        1188
Ser Ser Gly Leu Thr Gly Asp Ser His Ser Gln Asn Ile Leu Pro Val
320                 325                 330                 335

TCT GAG TGAAGGACCG CGCTCCTGCT GAAGAGTTTA GAATGAGGCA GCGGTGAGAA        1244
Ser Glu

GAAGGGTGGG AGGGCGTGGG GGCCCCTGGG TGGACACCAC CAGCCACCAG TCCCTGGCAT        1304

GCCCAGATGA TCCTGGTTCC CTGGCTTGTA GGGGCTCCAG AGCCTGCTTC CTGGTTCCTC        1364

AAGGGCAGAT ATTGGACACT TCCTTATTTG TCACCAAAGG AATGACTGTA GGCCGTGTGT        1424

TGGCCCTTCT TTCTAAGAAG CTGCTTTGAG CTCCTGGACT CACCTGAGGC TCCCTGGGGG        1484

ATGACACTCA GTTCTGTCAC TGTCAAGGAT GCAGAGAGCT GGTGGTAGGT GGGAAGCATG        1544

GTGTCCACCT GCCTGCTGAC CACTGGACGC TGCTCCATGC TGAAGAAAAG TGACAGTCTC        1604

CAGGGGACAT TTCAGCCATG CTGAAAGGGA GGCTGGCAGT GGTCATTGGC CCGGATCTAA        1664

CATGGCACCT CGTCTCCACA GGGTAGTGGT GGCTGCTTCA ACCCAAATAT TATTCAGCTG        1724
```

```
GTACTAACGA CATTGTGCCC AGCTGGGACT CTTGGGCTCT GTGCCTGAGG GAAAATGTTT    1784

CACAACTAGT GGCTGCCCAA TTGCTGCTGA CCAGTTGTCT TAGAAATGGT CAATTGGATT    1844

CAACTTTAGT CCTCTCCTTC CCCCTAAAAG CGAATGTTTG TGTGTGCAGA CAATCTTAGC    1904

ATGAAAATGG TTTAAATAGG CTGGTCCTAC ATGTATTAGG TTCTTTCAAG TTTGACTGGG    1964

AGGTCACCTT TTTCTGATTT ACAAGTCCTA ATTGTTGGAG CTCAGTAAAG GTAGGAGGAA    2024

GGTGGCTGGT TGGTCCTCCC TTCCCCCTGT TTGTGACCTG AATTTACAGG AAGTGTTTCA    2084

ACTTGTCTTA TGCATCTTAT CTGGCATGTC CTGGGAGATG GATGGGCAAG AACTGGCCTG    2144

AGCAGGGATT TTTGCCTTGA TTTTAAGTCA CTGGGTTCCA TTGTCCTGGC ACCTCCATTT    2204

CCTTAGTTTC TGTAAGCCTG TTAACAGAAA GTAGAGGCTA TTCAAGGTTA TCAAGAAAGT    2264

GCCCTGTGCT AATGATGAGA CAGTGAATTT TTTTTTTTTT CAGATGGGAG TTTCACTCTT    2324

ATTGCCCAGG CTAGAGTGCA ATGGTGCGAT CTAGGCTCAC CGCAACCTCT GCCTTCCAGG    2384

TTCAAGTGAT TAGAGACAGT GAAATTTTTA TGGAATACTG CACCTATAAA ACACATGCCA    2444

ATCTGTTAGC AGTCCTGACT TGATTTAATA AAAACCAAGG AGAGCCAAAA AAAAAAAAA    2504

AAAAAAAAAA AAAAAGGGCG GCCGCTCTAG AGGATCCAAG CTTACGTACG CGTGCATGCG    2564

ACGTCATAGC TCTTGGA                                                   2581

(2) INFORMATION FOR SEQ ID NO:2:

(i) SEQUENCE CHARACTERISTICS:
        (A) LENGTH: 337 amino acids
        (B) TYPE: amino acid
        (D) TOPOLOGY: linear (ii) MOLECULE TYPE: protein (xi) SEQUENCE DESCRIPTION: SEQ ID NO:2:

Met Asn Ser Trp Asp Ala Gly Leu Ala Gly Leu Leu Val Gly Thr Met
  1               5                  10                  15

Gly Val Ser Leu Leu Ser Asn Ala Leu Val Leu Cys Leu Leu His
             20                  25                  30

Ser Ala Asp Ile Arg Arg Gln Ala Pro Ala Leu Phe Thr Leu Asn Leu
         35                  40                  45

Thr Cys Gly Asn Leu Leu Cys Thr Val Val Asn Met Pro Leu Thr Leu
     50                  55                  60

Ala Gly Val Val Ala Arg Arg Gln Pro Ala Gly Asp Arg Leu Cys Arg
 65                  70                  75                  80

Leu Ala Ala Phe Leu Asp Thr Phe Leu Ala Ala Asn Ser Met Leu Ser
             85                  90                  95

Met Ala Ala Leu Ser Ile Asp Arg Trp Val Ala Val Phe Pro Leu
            100                 105                 110

Ser Tyr Arg Ala Lys Met Arg Leu Arg Asp Ala Ala Leu Met Val Ala
        115                 120                 125

Tyr Thr Trp Leu His Ala Leu Thr Phe Pro Ala Ala Ala Leu Ala Leu
    130                 135                 140

Ser Trp Leu Gly Phe His Gln Leu Tyr Ala Ser Cys Thr Leu Cys Ser
145                 150                 155                 160

Arg Arg Pro Asp Glu Arg Leu Arg Phe Ala Val Phe Thr Gly Ala Phe
                165                 170                 175

His Ala Leu Ser Phe Leu Leu Ser Phe Val Val Leu Cys Cys Thr Tyr
            180                 185                 190

Leu Lys Val Leu Lys Val Ala Arg Phe His Cys Lys Arg Ile Asp Val
        195                 200                 205
```

```
Ile Thr Met Gln Thr Leu Val Leu Leu Val Asp Leu His Pro Ser Val
    210                 215                 220

Arg Glu Arg Cys Leu Glu Glu Gln Lys Arg Arg Arg Gln Arg Ala Thr
225                 230                 235                 240

Lys Lys Ile Ser Thr Phe Ile Gly Thr Phe Leu Val Cys Phe Ala Pro
            245                 250                 255

Tyr Val Ile Thr Arg Leu Val Glu Leu Phe Ser Thr Val Pro Ile Gly
                260                 265                 270

Ser His Trp Gly Val Leu Ser Lys Cys Leu Ala Tyr Ser Lys Ala Ala
            275                 280                 285

Ser Asp Pro Phe Val Tyr Ser Leu Leu Arg His Gln Tyr Arg Lys Ser
    290                 295                 300

Cys Lys Glu Ile Leu Asn Arg Leu Leu His Arg Arg Ser Ile His Ser
305                 310                 315                 320

Ser Gly Leu Thr Gly Asp Ser His Ser Gln Asn Ile Leu Pro Val Ser
                325                 330                 335

Glu (2) INFORMATION FOR SEQ ID NO:3:

(i) SEQUENCE CHARACTERISTICS:
        (A) LENGTH: 1011 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1011

(xi) SEQUENCE DESCRIPTION: SEQ ID NO:3:

ATG AAC TCG TGG GAC GCG GGC CTG GCG GGG CTA CTG GTG GGC ACG ATG      48
Met Asn Ser Trp Asp Ala Gly Leu Ala Gly Leu Leu Val Gly Thr Met
1               5                   10                  15

GGC GTC TCG CTG CTG TCC AAC GCG CTG GTG CTG CTC TGC CTG CTG CAC      96
Gly Val Ser Leu Leu Ser Asn Ala Leu Val Leu Leu Cys Leu Leu His
            20                  25                  30

AGC GCG GAC ATC CGC CGC CAG GCG CCG GCG CTC TTC ACC CTG AAC CTC     144
Ser Ala Asp Ile Arg Arg Gln Ala Pro Ala Leu Phe Thr Leu Asn Leu
        35                  40                  45

ACG TGC GGG AAC CTG CTG TGC ACC GTG GTC AAC ATG CCG CTC ACG CTG     192
Thr Cys Gly Asn Leu Leu Cys Thr Val Val Asn Met Pro Leu Thr Leu
    50                  55                  60

GCC GGC GTC GTG GCG CGG CGG CAG CCG GCG GGC GAC CGC CTG TGC CGC     240
Ala Gly Val Val Ala Arg Arg Gln Pro Ala Gly Asp Arg Leu Cys Arg
65                  70                  75                  80

CTG GCT GCC TTC CTC GAC ACC TTC CTG GCT GCC AAC TCC ATG CTC AGC     288
Leu Ala Ala Phe Leu Asp Thr Phe Leu Ala Ala Asn Ser Met Leu Ser
                85                  90                  95

ATG GCC GCG CTC AGC ATC GAC CGC TGG GTG GCC GTG GTC TTC CCG CTG     336
Met Ala Ala Leu Ser Ile Asp Arg Trp Val Ala Val Val Phe Pro Leu
            100                 105                 110

AGC TAC CGG GCC AAG ATG CGC CTC CGC GAC GCG GCG CTC ATG GTG GCC     384
Ser Tyr Arg Ala Lys Met Arg Leu Arg Asp Ala Ala Leu Met Val Ala
        115                 120                 125

TAC ACG TGG CTG CAC GCG CTC ACC TTC CCA GCC GCC GCG CTC GCC CTG     432
Tyr Thr Trp Leu His Ala Leu Thr Phe Pro Ala Ala Ala Leu Ala Leu
    130                 135                 140
```

| | | |
|---|---|---|
| TCC TGG CTC GGC TTC CAC CAG CTG TAC GCC TCG TGC ACG CTG TGC AGC<br>Ser Trp Leu Gly Phe His Gln Leu Tyr Ala Ser Cys Thr Leu Cys Ser<br>145                       150                       155                    160 | 480 |
| CGG CGG CCG GAC GAG CGC CTG CGC TTC GCC GTC TTC ACT GGC GCC TTC<br>Arg Arg Pro Asp Glu Arg Leu Arg Phe Ala Val Phe Thr Gly Ala Phe<br>                        165                       170                    175 | 528 |
| CAC GCT CTC AGC TTC CTG CTC TCC TTC GTC GTG CTC TGC TGC ACG TAC<br>His Ala Leu Ser Phe Leu Leu Ser Phe Val Val Leu Cys Cys Thr Tyr<br>              180                       185                    190 | 576 |
| CTC AAG GTG CTC AAG GTG GCC CGC TTC CAT TGC AAG CGC ATC GAC GTG<br>Leu Lys Val Leu Lys Val Ala Arg Phe His Cys Lys Arg Ile Asp Val<br>       195                     200                    205 | 624 |
| ATC ACC ATG CAG ACG CTC GTG CTG CTG GTG GAC CTG CAC CCC AGT GTG<br>Ile Thr Met Gln Thr Leu Val Leu Leu Val Asp Leu His Pro Ser Val<br>210                       215                       220 | 672 |
| CGG GAA CGC TGT CTG GAG GAG CAG AAG CGG AGG CGA CAG CGA GCC ACC<br>Arg Glu Arg Cys Leu Glu Glu Gln Lys Arg Arg Arg Gln Arg Ala Thr<br>225                       230                       235                    240 | 720 |
| AAG AAG ATC AGC ACC TTC ATA GGG ACC TTC CTT GTG TGC TTC GCG CCC<br>Lys Lys Ile Ser Thr Phe Ile Gly Thr Phe Leu Val Cys Phe Ala Pro<br>              245                     250                    255 | 768 |
| TAT GTG ATC ACC AGG CTA GTG GAG CTC TTC TCC ACG GTG CCC ATC GGC<br>Tyr Val Ile Thr Arg Leu Val Glu Leu Phe Ser Thr Val Pro Ile Gly<br>            260                     265                    270 | 816 |
| TCC CAC TGG GGG GTG CTG TCC AAG TGC TTG GCG TAC AGC AAG GCC GCA<br>Ser His Trp Gly Val Leu Ser Lys Cys Leu Ala Tyr Ser Lys Ala Ala<br>275                       280                       285 | 864 |
| TCC GAC CCC TTT GTG TAC TCC TTA CTG CGA CAC CAG TAC CGC AAA AGC<br>Ser Asp Pro Phe Val Tyr Ser Leu Leu Arg His Gln Tyr Arg Lys Ser<br>            290                     295                    300 | 912 |
| TGC AAG GAG ATT CTG AAC AGG CTC CTG CAC AGA CGC TCC ATC CAC TCC<br>Cys Lys Glu Ile Leu Asn Arg Leu Leu His Arg Arg Ser Ile His Ser<br>305                       310                       315                    320 | 960 |
| TCT GGC CTC ACA GGC GAC TCT CAC AGC CAG AAC ATT CTG CCG GTG TCT<br>Ser Gly Leu Thr Gly Asp Ser His Ser Gln Asn Ile Leu Pro Val Ser<br>              325                     330                    335 | 1008 |
| GAG<br>Glu | 1011 |

(2) INFORMATION FOR SEQ ID NO:4:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:4:

Leu Leu Val Gly Thr Met Gly Val Ser Leu Leu Ser Asn Ala Leu Val
1               5                   10                 15

Leu Leu (2) INFORMATION FOR SEQ ID NO:5:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:5:

Leu Phe Thr Leu Asn Leu Thr Cys Gly Asn Leu Leu Cys Thr Val Val
1               5                   10                  15

Asn Met Pro Leu
            20

(2) INFORMATION FOR SEQ ID NO:6:

(i) SEQUENCE CHARACTERISTICS:
            (A) LENGTH: 23 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:6:

Arg Leu Ala Ala Phe Leu Asp Thr Phe Leu Ala Ala Asn Ser Met Leu
1               5                   10                  15

Ser Met Ala Ala Leu Ser Ile
            20

(2) INFORMATION FOR SEQ ID NO:7:

(i) SEQUENCE CHARACTERISTICS:
            (A) LENGTH: 26 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:7:

Arg Asp Ala Ala Leu Met Val Ala Tyr Thr Trp Leu His Ala Leu Thr
1               5                   10                  15

Phe Pro Ala Ala Ala Leu Ala Leu Ser Trp
            20                  25

(2) INFORMATION FOR SEQ ID NO:8:

(i) SEQUENCE CHARACTERISTICS:
            (A) LENGTH: 22 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:8:

Phe Ala Val Phe Thr Gly Ala Phe His Ala Leu Ser Phe Leu Leu Ser
1               5                   10                  15

Phe Val Val Leu Cys Cys
            20

(2) INFORMATION FOR SEQ ID NO:9:

(i) SEQUENCE CHARACTERISTICS:
            (A) LENGTH: 19 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:9:

Ile Gly Thr Phe Leu Val Cys Phe Ala Pro Tyr Val Ile Thr Arg Leu
1               5                  10                  15

Val Glu Leu (2) INFORMATION FOR SEQ ID NO:10:

(i) SEQUENCE CHARACTERISTICS:
            (A) LENGTH: 21 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:10:

Lys Cys Leu Ala Tyr Ser Lys Ala Ala Ser Asp Pro Phe Val Tyr Ser
1               5                  10                  15

Leu Leu Arg His Gln
            20

(2) INFORMATION FOR SEQ ID NO:11:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:11:

CGGGGCGCGC ACCATG                                                    16

(2) INFORMATION FOR SEQ ID NO:12:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:12:

CACCATGAAC TCGTGGG                                                   17

(2) INFORMATION FOR SEQ ID NO:13:

(i) SEQUENCE CHARACTERISTICS:
            (A) LENGTH: 16 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:13:

TGAAGGACCG CGCTCC                                                    16

(2) INFORMATION FOR SEQ ID NO:14:

(i) SEQUENCE CHARACTERISTICS:
            (A) LENGTH: 16 base pairs
            (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO:14:

TCTGAGTGAA GGACCG                                                      16
```

ISOLATED NUCLEIC ACID MOLECULES ENCODING A G-PROTEIN COUPLED RECEPTOR SHOWING HOMOLOGY TO THE 5HT FAMILY OF RECEPTORS

BACKGROUND OF THE INVENTION

G-protein coupled receptors (GPCRs) are one of the major class of proteins that are responsible for transducing a signal within a cell. GPCRs are proteins that have seven transmembrane domains. Upon binding of a ligand to the extracellular domain of a GPCR, a signal is transduced within the cell which results in a change in a biological or physiological property of the cell.

GPCRs, along with G-proteins and effectors (intracellular enzymes and channels which are modulated by G-proteins), are the components of a modular signaling system that connects the state of intracellular second messengers to extracellular inputs. These genes and gene-products are potential causative agents of disease (Spiegel et al. (1993) *J. Clin. Invest.* 92:1119–1125; McKusick and Amberger (1993) *J. Med. Genet.* 30:1–26). Specific defects in the rhodopsin gene and the V2 vasopressin receptor gene have been shown to cause various forms of autosomal dominant and autosomal recessive retinitis pigmentosa (see Nathans et al. (1992) *Annu. Rev. Genet.* 26:403–424), nephrogenic diabetes insipidus (Holtzman et al. (1993) *Hum. Mol. Genet.* 2:1201–1204 and references therein). These receptors are of critical importance to both the central nervous system and peripheral physiological processes. Evolutionary analyses suggest that the ancestor of these proteins originally developed in concert with complex body plans and nervous systems.

The GPCR protein superfamily now contains over 250 types of paralogues, receptors that represent variants generated by gene duplications (or other processes), as opposed to orthologues, the same receptor from different species. The superfamily can be broken down into five families: Family I, receptors typified by rhodopsin and the beta2-adrenergic receptor and currently represented by over 200 unique members (reviewed by Dohlman et al. (1991) *Annu. Rev. Biochem.* 60:653–688 and references therein); Family II, the recently characterized parathyroid hormone/calcitonin/secretin receptor family (Juppner et al. (1991) *Science* 254:1024–1026; Lin et al. (1991) *Science* 254:1022–1024); Family III, the metabotropic glutamate receptor family in mammals (Nakanishi (1992) *Science* 258:597–603); Family IV, the cAMP receptor family, important in the chemotaxis and development of *D. discoideum* (Klein et al. (1988) *Science* 241:1467–1472); and Family V, the fingal mating pheromone receptors such as STE2 (reviewed by Kurjan (1992) *Annu. Rev. Biochem.* 61:1097–1129).

In addition to these groups of GPCRs, there are a small number of other proteins which present seven putative hydrophobic segments and appear to be unrelated to GPCRs; however, they have not been shown to couple to G-proteins. Drosophila express a photoreceptor-specific protein bride of sevenless (boss), a seven-transmembrane-segment protein which has been extensively studied and does not show evidence of being a GPCR (Hart et al. (1993) *Proc. Natl. Acad. Sci. USA* 90:5047–5051 (1993)). The gene frizzled (fz) in Drosophila is also thought to be a protein with seven transmembrane segments. Like boss, fz has not been shown to couple to G-proteins (Vinson et al. (1989) *Nature* 338:263–264).

G proteins represent a family of heterotrimeric proteins composed of $\alpha$, $\beta$ and $\gamma$ subunits, which bind guanine nucleotides. These proteins are usually linked to cell surface receptors, e.g., receptors containing seven transmembrane domains, such as the ligand receptors. Following ligand binding to the receptor, a conformational change is transmitted to the G protein, which causes the $\alpha$-subunit to exchange a bound GDP molecule for a GTP molecule and to dissociate from the $\beta\gamma$-subunits. The GTP-bound form of the $\alpha$-subunit typically functions as an effector-modulating moiety, leading to the production of second messengers, such as cyclic AMP (e.g., by activation of adenylate cyclase), diacylglycerol or inositol phosphates. Greater than 20 different types of $\alpha$-subunits are known in man, which associate with a smaller pool of $\beta$ and $\gamma$ subunits. Examples of mammalian G proteins include Gi, Go, Gq, Gs and Gt. G proteins are described extensively in Lodish H. et al. Molecular Cell Biology, (Scientific American Books Inc., New York, N.Y., 1995), the contents of which are incorporated herein by reference.

GPCRs are a major target for drug action and development. Accordingly, it is valuable to the field of pharmaceutical development to identify and characterize previously unknown GPCRs. The present invention advances the state of the art by providing a previously unidentified GPCR which is expressed predominantly in the brain.

SUMMARY OF THE INVENTION

The present invention is based on the identification of a novel G-protein coupled receptor (GPCR) that is expressed predominantly in the brain and nucleic acid molecules that encoded the GPCR, referred to herein as the flh2882 protein and flh2882 gene respectively. Based on this identification, the present invention provides: 1) isolated flh2882 protein; 2) isolated nucleic acid molecules that encode an flh2882 protein; 3) antibodies that selectively bind to the flh2882 protein; 4) methods of isolating allelic variants of the flh2882 protein and gene; 5) methods of identifying cells and tissues that express the flh2882 protein/gene; 6) methods of identifying agents and cellular compounds that bind to the flh2882 protein; 7) methods of identifying agents that modulate the expression of the flh2882 gene; and 8) methods of modulating the activity of the flh2882 protein in a cell or organism.

BRIEF DESCRIPTION OF THE DRAWINGS

FIG. 1 depicts the human flh2882 gene sequence (SEQ ID NO:1).

FIG. 2 depicts the coding region of the human flh2882 gene without the 5' and 3' untranslated regions (SEQ ID NO:3).

FIG. 3 depicts the amino acid sequence of the human flh2882 protein (SEQ ID NO:2).

DETAILED DESCRIPTION OF THE INVENTION

The present invention is based on the discovery of a novel G-protein coupled receptor (GPCR) molecule that is expressed predominantly in the brain, the flh2882 protein, and nucleic acid molecules that encode the flh2882 protein, the flh2882 gene or flh2882 nucleic acid molecule. Specifically, an EST was first identified in a public database that had low homology to G-protein coupled receptors. PCR primers were then designed based on this sequence and a cDNA was identified by screening a human fetal cDNA library (See Example 1). Positive clones were sequenced and contigs were assembled. Analysis of the assembled sequence revealed that the cloned cDNA molecule encoded a GPCR, denoted herein as the flh2882 protein. The flh2882 protein is a GPCR and plays a role in and function in signaling pathways within cells that express the flh2882 protein, particularly brain cells.

Various aspects of the invention are described in further detail in the following subsections:

I. Isolated flh2882 Protein

The present invention provides isolated flh2882 protein as well as peptide fragments of an flh2882 protein.

As used herein, a protein is said to be "isolated" or "purified" when it is substantially free of cellular when it is isolated from recombinant and non-recombinant cells, or free of chemical precursors or other chemicals when it is chemically synthesized. The language "substantially free of cellular material" includes preparations of flh2882 protein in which the protein is separated from cellular components of the cells in which it is naturally or recombinantly produced. In one embodiment, the language "substantially free of cellular material" includes preparations of an flh2882 protein having less than about 30% (by dry weight) of non-flh2882 protein (also referred to herein as a "contaminating protein"), more preferably less than about 20% of non-flh2882 protein, still more preferably less than about 10% of non-flh2882 protein, and most preferably less than about 5% non-flh2882 protein. When the flh2882 protein or biologically active fragment thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of flh2882 protein in which the protein is separated from chemical precursors or other chemicals that are involved in the synthesis of the protein. In one embodiment, the language "substantially free of chemical precursors or other chemicals" includes preparations of flh2882 protein having less than about 30% (by dry weight) of chemical precursors or non-flh2882 chemicals, more preferably less than about 20% chemical precursors or non-flh2882 chemicals, still more preferably less than about 10% chemical precursors or non-flh2882 chemicals, and most preferably less than about 5% chemical precursors or non-flh2882 chemicals. In preferred embodiments, isolated proteins or biologically active fragments thereof lack contaminating proteins from the same animal from which the flh2882 protein is derived. Typically, such proteins are produced by recombinant expression of, for example, a human flh2882 protein in a non-human cell.

As used herein, an flh2882 protein is defined as a protein that comprises: 1) the amino acid sequence shown in SEQ ID NO:2 or an amino acid sequence which is encoded by the nucleotide sequence of the DNA insert of the plasmid deposited with ATCC as Accession No. 98914, hereinafter human flh2882 protein; 2) functional and non-functional naturally occurring allelic variants of human flh2882 protein; 3) recombinantly produced variants of human flh2882 protein; and 4) flh2882 proteins isolated from organisms other than humans (orthologues of human flh2882 protein.)

As used herein, an allelic variant of human flh2882 protein is defined as: 1) a protein isolated from human cells or tissues; 2) a protein encoded by the same genetic locus as that encoding the human flh2882 protein; and 3) a protein that contains substantially homology to human flh2882.

As used herein, two proteins are substantially homologous when the amino acid sequence of the two protein (or a region of the proteins) are at least about 60–65%, typically at least about 70–75%, more typically at least about 80–85%, and most typically at least about 90–95% or more homologous to each other. To determine the percent homology of two amino acid sequences (e.g., SEQ ID NO:2 and an allelic variant thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., SEQ ID NO:2) is occupied by the same amino acid residue or nucleotide as the corresponding position in the other sequence (e.g., an allelic variant of the human flh2882 protein), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

Allelic variants of human flh2882 include both functional and non-functional flh2882 proteins. Functional allelic variants are naturally occurring amino acid sequence variants of the human flh2882 protein that maintain the ability to bind an flh2882 ligand and transduce a signal within a cell. Functional allelic variants will typically contain only conservative substitution of one or more amino acids of SEQ ID NO:2 or substitution, deletion or insertion of non-critical residues in non-critical regions of the protein.

Non-functional allelic variants are naturally occurring amino acid sequence variants of human flh2882 protein that do not have the ability to either bind ligand and/or transduce a signal within a cell. Non-functional allelic variants will typically contain a non-conservative substitution, a deletion, or insertion or premature truncation of the amino acid sequence of SEQ. ID. NO:2 or a substitution, insertion or deletion in critical residues or critical regions.

The present invention further provides non-human orthologues of human flh2882 protein. Orthologues of human flh2882 protein are proteins that are isolated from non-human organisms and possess the same ligand binding and signaling capabilities of the human flh2882 protein. Orthologues of the human flh2882 protein can readily be identified as comprising an amino acid sequence that is substantially homologous to SEQ ID NO:2.

The flh2882 protein is a GPCR that participates in signaling pathways within cells. As used herein, a signaling pathway refers to the modulation (e.g., stimulated or inhibited) of a cellular function/activity upon the binding of a ligand to the GPCR (flh2882 protein). Examples of such functions include mobilization of intracellular molecules that participate in a signal transduction pathway, e.g., phosphatidylinositol 4,5-bisphosphate ($PIP_2$), inositol 1,4,5-triphosphate ($IP_3$) or adenylate cyclase; polarization of the plasma membrane; production or secretion of molecules; alteration in the structure of a cellular component; cell proliferation, e.g., synthesis of DNA; cell migration; cell differentiation; and cell survival. Since the flh2882 protein is expressed substantially in the brain, examples of cells participating in an flh2882 signaling pathway include neural cells, e.g., peripheral nervous system and central nervous system cells such as brain cells, e.g., limbic system cells, hypothalamus cells, hippocampus cells, substantia nigra cells, cortex cells, brain stem cells, neocortex cells, basal ganglion cells, caudate putamen cells, olfactory tubercle cells, and superior colliculi cells.

Depending on the type of cell, the response mediated by the flh2882 protein/ligand binding may be different. For example, in some cells, binding of a ligand to an flh2882 protein may stimulate an activity such as adhesion, migration, differentiation, etc. through phosphatidylinositol or cyclic AMP metabolism and turnover while in other cells, the binding of the ligand to the flh2882 protein will produce a different result. Regardless of the cellular activity modulated by flh2882, it is universal that the flh2882 protein is a GPCR and interacts with a "G protein" to produce one or more secondary signals in a variety of intracellular signal transduction pathways, e.g., through phosphatidylinositol or cyclic AMP metabolism and turnover, in a cell. G proteins represent a family of heterotrimeric proteins composed of α, β and γ subunits, which bind guanine nucleotides. These proteins are usually linked to cell surface receptors, e.g., receptors containing seven transmembrane domains, such as the ligand receptors. Following ligand binding to the receptor, a conformational change is transmitted to the G protein, which causes the α-subunit to exchange a bound GDP molecule for a GTP molecule and to dissociate from the βγ-subunits. The GTP-bound form of the α-subunit typically functions as an effector-modulating moiety, leading to the production of second messengers, such as cyclic AMP (e.g., by activation of adenylate cyclase), diacylglycerol or inositol phosphates. Greater than 20 different types of α-subunits are known in man, which associate with a smaller pool of β and γ subunits. Examples of mammalian G proteins include Gi, Go, Gq, Gs and Gt. G proteins are described extensively in Lodish H. et al. Molecular Cell Biology, (Scientific American Books Inc., New York, N.Y., 1995), the contents of which are incorporated herein by reference.

As used herein, "phosphatidylinositol turnover and metabolism" refers to the molecules involved in the turnover and metabolism of phosphatidylinositol 4,5-bisphosphate ($PIP_2$) as well as to the activities of these molecules. $PIP_2$ is a phospholipid found in the cytosolic leaflet of the plasma membrane. Binding of a ligand to the flh2882 activates, in some cells, the plasma-membrane enzyme phospholipase C that in turn can hydrolyze $PIP_2$ to produce 1,2-diacylglycerol (DAG) and inositol 1,4,5-triphosphate ($IP_3$). Once formed $IP_3$ can diffuse to the endoplasmic reticulum surface where it can bind an $IP_3$ receptor, e.g., a calcium channel protein containing an $IP_3$ binding site. $IP_3$ binding can induce opening of the channel, allowing calcium ions to be released into the cytoplasm. $IP_3$ can also be phosphorylated by a specific kinase to form inositol 1,3,4,5-tetraphosphate ($IP_4$), a molecule which can cause calcium entry into the cytoplasm from the extracellular medium. $IP_3$ and $IP_4$ can subsequently be hydrolyzed very rapidly to the inactive products inositol 1,4-biphosphate ($IP_2$) and inositol 1,3,4-triphosphate, respectively. These inactive products can be recycled by the cell to synthesize $PIP_2$. The other second messenger produced by the hydrolysis of $PIP_2$, namely 1,2-diacylglycerol (DAG), remains in the cell membrane where it can serve to activate the enzyme protein kinase C. Protein kinase C is usually found soluble in the cytoplasm of the cell, but upon an increase in the intracellular calcium concentration, this enzyme can move to the plasma membrane where it can be activated by DAG. The activation of protein kinase C in different cells results in various cellular responses such as the phosphorylation of glycogen synthase, or the phosphorylation of various transcription factors, e.g., NF-kB. The language "phosphatidylinositol activity", as used herein, refers to an activity of $PIP_2$ or one of its metabolites.

Another signaling pathway in which the flh2882 protein may participate is the cAMP turnover pathway. As used herein, "cyclic AMP turnover and metabolism" refers to the molecules involved in the turnover and metabolism of cyclic AMP (cAMP) as well as to the activities of these molecules. Cyclic AMP is a second messenger produced in response to ligand induced stimulation of certain G protein coupled receptors. In the ligand signaling pathway, binding of ligand to a ligand receptor can lead to the activation of the enzyme adenylate cyclase, which catalyzes the synthesis of cAMP. The newly synthesized cAMP can in turn activate a cAMP-dependent protein kinase. This activated kinase can phosphorylate a voltage-gated potassium channel protein, or an associated protein, and lead to the inability of the potassium channel to open during an action potential. The inability of the potassium channel to open results in a decrease in the outward flow of potassium, which normally repolarizes the membrane of a neuron, leading to prolonged membrane depolarization.

The present invention further provides fragments of flh2882 proteins. As used herein, a fragment comprises at least 8 contiguous amino acids from an flh2882 protein. Preferred fragments are fragments that possess one or more of the biological activities of the flh2882 protein, for example the ability to bind to a G-protein, as well as fragments that can be used as an immunogen to generate anti-flh2882 antibodies.

Biologically active fragments of the flh2882 protein include peptides comprising amino acid sequences derived from the amino acid sequence of an flh2882 protein, e.g., the amino acid sequence shown in SEQ ID NO:2 or the amino acid sequence of a protein homologous to the flh2882 protein, which include less amino acids than the full length flh2882 protein or the full length protein which is homologous to the flh2882 protein, and exhibit at least one activity of the flh2882 protein. Typically, biologically active fragments (peptides, e.g., peptides which are, for example, 5, 10, 15, 20, 30, 35, 36, 37, 38, 39, 40, 50, 100 or more amino acids in length) comprise a domain or motif, e.g., a transmembrane domain or G-protein binding domain.

The isolated flh2882 proteins can be purified from cells that naturally express the protein, purified from cells that have been altered to express the flh2882 protein, or synthesized using known protein synthesis methods. Preferably, as described below, the isolated flh2882 protein is produced by recombinant DNA techniques. For example, a nucleic acid molecule encoding the protein is cloned into an expression vector (as described above), the expression vector is introduced into a host cell (as described above) and the flh2882 protein is expressed in the host cell. The flh2882 protein can then be isolated from the cells by an appropriate purification scheme using standard protein purification techniques. Alternative to recombinant expression, the flh2882 protein or fragment can be synthesized chemically using standard peptide synthesis techniques. Lastly, native flh2882 protein can be isolated from cells that naturally express the flh2882 protein (e.g., hippocampal cells, or substantia nigra cells).

The present invention further provides flh2882 chimeric or fusion proteins. As used herein, an flh2882 "chimeric protein" or "fusion protein" comprises an flh2882 protein operatively linked to a non-flh2882 protein. An "flh2882 protein" refers to a protein having an amino acid sequence corresponding to an flh2882 protein, whereas a "non-flh2882 protein" refers to a heterologous protein having an amino acid sequence corresponding to a protein which is not substantially homologous to the flh2882 protein, e.g., a protein which is different from the flh2882 protein. Within the context of fusion proteins, the term "operatively linked" is intended to indicate that the flh2882 protein and the non-flh2882 protein are fused in-frame to each other. The non-flh2882 protein can be fused to the N-terminus or C-terminus of the flh2882 protein. For example, in one embodiment the fusion protein is a GST-flh2882 fusion protein in which the flh2882 sequences are fused to the C-terminus of the GST sequences. Other types of fusion proteins include, but are not limited to, enzymatic fusion proteins, for example beta-galactosidase fusions, yeast two-hybrid GAL fusions, poly-His fusions and Ig fusions. Such fusion proteins, particularly poly-His fusions, can facilitate the purification of recombinant flh2882 protein. In another embodiment, the fusion protein is an flh2882 protein containing a heterologous signal sequence at its N-terminus. In certain host cells (e.g., mammalian host cells), expression and/or secretion of an flh2882 protein can be increased by using a heterologous signal sequence.

Preferably, an flh2882 chimeric or fusion protein is produced by standard recombinant DNA techniques. For example, DNA fragments coding for the different protein sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, Current Protocols in Molecular Biology, eds. Ausubel et al. John Wiley & Sons: 1992). Moreover, many expression vectors are commercially available that already encode a fusion moiety (e.g., a GST protein). An flh2882-encoding nucleic acid can be cloned into such an expression vector such that the fusion moiety is linked in-frame to the flh2882 protein.

The present invention also provides altered forms of flh2882 proteins that have been generated using recombinant DNA or mutagenic methods/agents. Altered forms of an flh2882 protein can be generated by mutagenesis, e.g., discrete point mutation or truncation of the flh2882 protein and recombinant DNA method that are well known in the art.

II. Antibodies that Bind to an flh2882 Protein

The present invention further provides antibodies that selectively bind to an flh2882 protein. As used herein, an antibody is said to selectively bind to an flh2882 protein when the antibody binds to flh2882 proteins and does not substantially bind to unrelated proteins. A skilled artisan will readily recognize that an antibody may be considered to substantially bind an flh2882 protein even if it binds to proteins that share homology with a fragment or domain of the flh2882 protein.

The term "antibody" as used herein refers to immunoglobulin molecules and immunologically active fragments of immunoglobulin molecules, i.e., molecules that contain an antigen binding site which specifically binds (immunoreacts with) an antigen, such as flh2882. Examples of immunologically active fragments of immunoglobulin molecules include F(ab) and F(ab')$_2$ fragments which can be generated by treating the antibody with an enzyme such as pepsin. The invention provides polyclonal and monoclonal antibodies that bind flh2882. The term "monoclonal antibody" or "monoclonal antibody composition", as used herein, refers to a population of antibody molecules that contain only one species of an antigen binding site capable of immunoreacting with a particular epitope of flh2882. A monoclonal antibody composition thus typically displays a single binding affinity for a particular flh2882 protein with which it immunoreacts.

To generate anti-flh2882 antibodies, an isolated flh2882 protein, or a fragment thereof, is used as an immunogen to generate antibodies that bind flh2882 using standard techniques for polyclonal and monoclonal antibody preparation. The full-length flh2882 protein can be used or, alternatively, an antigenic peptide fragment of flh2882 can be used as an immunogen. An antigenic fragment of the flh2882 protein will typically comprises at least 8 contiguous amino acid residues of an flh2882 protein, e.g. 8 contiguous amino acids from SEQ ID NO:2. Preferably, the antigenic peptide comprises at least 10 amino acid residues, more preferably at least 15 amino acid residues, even more preferably at least 20 amino acid residues, and most preferably at least 30 amino acid residues of an flh2882 protein. Preferred fragments for generating anti-flh2882 antibodies are regions of flh2882 that are located on the surface of the protein, e.g., hydrophilic regions.

An flh2882 immunogen typically is used to prepare antibodies by immunizing a suitable subject, (e.g., rabbit, goat, mouse or other mammal) with the immunogen. An appropriate immunogenic preparation can contain, for example, recombinantly expressed flh2882 protein or a chemically synthesized flh2882 peptide. The preparation can further include an adjuvant, such as Freund's complete or incomplete adjuvant, or similar immunostimulatory agent. Immunization of a suitable subject with an immunogenic flh2882 preparation induces a polyclonal anti-flh2882 antibody response.

Polyclonal anti-flh2882 antibodies can be prepared as described above by immunizing a suitable subject with an flh2882 immunogen. The anti-flh2882 antibody titer in the immunized subject can be monitored over time by standard techniques, such as with an enzyme linked immunosorbent assay (ELISA) using immobilized flh2882. If desired, the antibody molecules directed against flh2882 can be isolated from the mammal (e.g., from the blood) and further purified by well known techniques, such as protein A chromatography to obtain the IgG fraction. At an appropriate time after immunization, e.g., when the anti-flh2882 antibody titers are highest, antibody-producing cells can be obtained from the subject and used to prepare monoclonal antibodies by standard techniques, such as the hybridoma technique originally described by Kohler and Milstein (1975) Nature 256:495–497) (see also, Brown et al. (1981) J. Immunol. 127:539–46; Brown et al. (1980) J. Biol. Chem. 255:4980–83; Yeh et al. (1976) PNAS 76:2927–31; and Yeh et al. (1982) Int. J. Cancer 29:269–75), the more recent human B cell hybridoma technique (Kozbor et al. (1983) Immunol Today 4:72), the EBV-hybridoma technique (Cole et al. (1985), Monoclonal Antibodies and Cancer Therapy, Alan R. Liss, Inc., pp. 77–96) or trioma techniques. The technology for producing monoclonal antibody hybridomas is well known (see generally R. H. Kenneth, in Monoclonal Antibodies: A New Dimension In Biological Analyses, Plenum Publishing Corp., New York, N.Y. (1980); E. A. Lerner (1981) Yale J. Biol. Med., 54:387–402; M. L. Gefter et al. (1977) Somatic Cell Genet. 3:231–36). Briefly, an immortal cell line (typically a myeloma) is fused to lymphocytes (typically splenocytes) from a mammal immunized with an flh2882 immunogen as described above, and the culture supernatants of the resulting hybridoma cells are screened to identify a hybridoma producing a monoclonal antibody that binds flh2882.

Any of the many well known protocols used for fusing lymphocytes and immortalized cell lines can be applied for the purpose of generating an anti-flh2882 monoclonal antibody (see, e.g., G. Galfre et al. (1977) Nature 266:55052; Gefter et al. Somatic Cell Genet., cited supra; Lerner, Yale J. Biol. Med., cited supra; Kenneth, Monoclonal Antibodies, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind flh2882, e.g., using a standard ELISA assay.

Alternative to preparing monoclonal antibody-secreting hybridomas, a monoclonal anti-flh2882 antibody can be identified and isolated by screening a recombinant combinatorial immunoglobulin library (e.g., an antibody phage display library) with flh2882 to thereby isolate immunoglobulin library members that bind flh2882. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) Bio/Technology 9:1370–1372; Hay et al. (1992) Hum. Antibod. Hybridomas 3:81–85; Huse et al. (1989) Science 246:1275–1281; Griffiths et al. (1993) EMBO J 12:725–734; Hawkins et al. (1992) J. Mol. Biol. 226:889–896; Clarkson et al. (1991) Nature 352:624–628; Gram et al. (1992) PNAS 89:3576–3580; Garrad et al. (1991) Bio/Technology 9:1373–1377; Hoogenboom et al. (1991) Nuc. Acid Res. 19:4133–4137; Barbas et al. (1991) PNAS 88:7978–7982; and McCafferty et al. Nature (1990) 348:552–554.

Additionally, recombinant anti-flh2882 antibodies, such as chimeric and humanized monoclonal antibodies, comprising both human and non-human fragments, which can be made using standard recombinant DNA techniques, are within the scope of the invention. Such chimeric and humanized monoclonal antibodies can be produced by recombinant DNA techniques known in the art, for example using methods described in Robinson et al. PCT International Application No. PCT/US86/02269; Akira, et al. European Patent Application 184,187; Taniguchi, M., European Patent Application 171,496; Morrison et al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) Science 240:1041–1043; Liu et al. (1987) PNAS 84:3439–3443; Liu et al. (1987) J. Immunol. 139:3521–3526; Sun et al. (1987) PNAS 84:214–218; Nishimura et al. (1987) Canc. Res. 47:999–1005; Wood et al. (1985) Nature 314:446–449; and Shaw et al. (1988) J. Natl. Cancer Inst. 80:1553–1559); Morrison, S. L. (1985) Science 229:1202–1207; Oi et al. (1986) BioTechniques 4:214; Winter U.S. Pat. No. 5,225,539; Jones et al. (1986) Nature 321:552–525; Verhoeyan et al. (1988) Science 239:1534; and Beidler et al. (1988) J. Immunol. 141:4053–4060.

An anti-flh2882 antibody (e.g., monoclonal antibody) can be used to isolate flh2882 proteins by standard techniques, such as affinity chromatography or immunoprecipitation. An anti-flh2882 antibody can facilitate the purification of natural flh2882 protein from cells and recombinantly produced flh2882 protein expressed in host cells. Moreover, an anti-flh2882 antibody can be used to detect flh2882 protein (e.g., in a cellular lysate or cell supernatant) in order to evaluate the abundance and pattern of expression of the flh2882 protein. The detection of circulating fragments of an flh2882 protein can be used to identify flh2882 protein turnover in a subject. Anti-flh2882 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Isolated flh2882 Nucleic Acid Molecules

The present invention further provides isolated nucleic acid molecules that encode an flh2882 protein, hereinafter the flh2882 gene or flh2882 nucleic acid molecule, as well as fragments of an flh2882 gene.

As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

As used herein, an "isolated" nucleic acid molecule is one that is separated from other nucleic acid molecules that are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated flh2882 nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a substantia nigra cell). Moreover, an "isolated" nucleic acid molecule, such as a cDNA molecule, can be substantially free of other cellular material, or culture medium when produced by recombinant techniques, or chemical precursors or other chemicals when chemically synthesized. However, the flh2882 nucleic acid molecule can be fused to other protein encoding or regulatory sequences and still be considered isolated.

The isolated nucleic acid molecules of the present invention encode an flh2882 protein. As described above, an flh2882 protein is defined as a protein comprising the amino acid sequence depicted in SEQ ID NO:2 (human flh2882 protein), allelic variants of human flh2882 protein, and orthologues of the human flh2882 protein. A preferred flh2882 nucleic acid molecule comprises the nucleotide sequence shown in SEQ ID NO:1 or the nucleotide sequence of the DNA insert of the plasmid deposited with ATCC (American Type Culture Collection, 10801 University Boulevard, Manassas, Va. 20110-2209) on Oct. 2, 1998, as Accession No. 98914. The sequence of SEQ ID NO:1 corresponds to the human flh2882 cDNA. This cDNA comprises sequences encoding the human flh2882 protein (i.e., "the coding region", from nucleotides 184 to 1194 of SEQ ID NO:1), as well as 5' untranslated sequences (nucleotides 1 to 183 of SEQ ID NO:1) and 3' untranslated sequences (nucleotides 1195 to 2581 of SEQ ID NO:1). Alternatively, the nucleic acid molecule can comprise only the coding region of SEQ ID NO: 1 (e.g., nucleotides 184 to 1194 shown separately as SEQ ID NO:3).

The human flh2882 gene is approximately 2581 nucleotides in length and encodes a full length protein having a molecular weight of approximately 38.7 KDa and which is approximately 337 amino acid residues in length. The human flh2882 protein is expressed primarily in the brain, particularly the substantia nigra. Based on structural analysis, amino acid residues 11–28 (SEQ ID NO:4), 43–62 (SEQ ID NO:5), 80–102 (SEQ ID NO:6), 121–146 (SEQ ID NO:7), 169–190 (SEQ ID NO:8), 247–265 (SEQ ID NO:9), and 280–300 (SEQ ID NO:10) comprise transmembrane domains. As used herein, the term "transmembrane domain" refers to a structural amino acid motif which includes a hydrophobic helix that spans the plasma membrane.

The invention further encompasses nucleic acid molecules that differ from the nucleotide sequence shown in SEQ ID NO:1 (and fragments thereof) due to degeneracy of the genetic code and thus encode the same flh2882 protein as that encoded by the nucleotide sequence shown in SEQ ID NO:1.

In another preferred embodiment, an isolated nucleic acid molecule of the invention comprises a nucleic acid molecule which is a complement of the nucleotide sequence shown in SEQ ID NO:1, the nucleotide sequence of the DNA insert of the plasmid deposited with ATCC as Accession No. 98914, or a fragment of either of these nucleotide sequences. A nucleic acid molecule which is complementary to the nucleotide sequence shown in SEQ ID NO:1 is one which is sufficiently complementary to the nucleotide sequence shown in SEQ ID NO:1 such that it can hybridize to the nucleotide sequence shown in SEQ ID NO:1, thereby forming a stable duplex.

Orthologues and allelic variants of the human flh2882 gene can readily be identified using methods well known in the art. Allelic variants and orthologues of the human flh2882 gene will comprise a nucleotide sequence that is at least about 60–65%, typically at least about 70–75%, more typically at least about 80–85%, and most typically at least about 90–95% or more homologous to the nucleotide sequence shown in SEQ ID NO:1, or to the nucleotide sequence of the DNA insert of the plasmid deposited with ATCC as Accession No. 98914, or a fragment of these nucleotide sequences. Such nucleic acid molecules can readily be identified as being able to hybridize, preferably under stringent conditions, to the nucleotide sequence shown in SEQ ID NO:1, or the nucleotide sequence of the DNA insert of the plasmid deposited with ATCC as Accession No. 98914, or a fragment of either of these nucleotide sequences.

Moreover, the nucleic acid molecule of the invention can comprise only a fragment of the coding region of an flh2882 gene, such as a fragment of SEQ ID NO:1. The nucleotide sequence determined from the cloning of the human flh2882 gene allows for the generation of probes and primers designed for use in identifying and/or cloning flh2882 gene homologues from other cell types, e.g., from other tissues, as well as flh2882 gene orthologues from other mammals. A probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of SEQ ID NO:1 sense, an anti-sense sequence of SEQ ID NO:1, or naturally occurring mutants thereof. Primers based on the nucleotide sequence in SEQ ID NO:1 can be used in PCR reactions to clone flh2882 gene homologues. Probes based on the flh2882 nucleotide sequence can be used to detect transcripts or genomic sequences encoding the same or homologous proteins. In preferred embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress an flh2882 protein, such as by measuring a level of an flh2882-encoding nucleic acid in a sample of cells from a subject e.g., detecting flh2882 mRNA levels or determining whether a genomic flh2882 gene has been mutated or deleted.

In addition to the flh2882 nucleotide sequence shown in SEQ ID NO:1, it will be appreciated by those skilled in the art that DNA sequence polymorphisms that lead to changes in the amino acid sequences of an flh2882 protein may exist within a population (e.g., the human population). Such genetic polymorphism in the flh2882 gene may exist among individuals within a population due to natural allelic variation. As used herein, the terms "gene" and "recombinant gene" refer to nucleic acid molecules comprising an open reading frame encoding an flh2882 protein, preferably a mammalian flh2882 protein. Such natural allelic variations can typically result in 1–5% variance in the nucleotide sequence of the flh2882 gene. Any and all such nucleotide variations and resulting amino acid polymorphisms in an flh2882 gene that are the result of natural allelic variation are intended to be within the scope of the invention. Such allelic variation includes both active allelic variants as well as non-active or reduced activity allelic variants, the later two types typically giving rise to a pathological disorder. Moreover, nucleic acid molecules encoding flh2882 proteins from other species, and thus which have a nucleotide sequence which differs from the human sequence of SEQ ID NO:1, are intended to be within the scope of the invention. Nucleic acid molecules corresponding to natural allelic variants and non-human orthologues of the human flh2882 cDNA of the invention can be isolated based on their homology to the human flh2882 nucleic acid disclosed herein using the human cDNA, or a fragment thereof, as a hybridization probe according to standard hybridization techniques under stringent hybridization conditions.

Accordingly, in another embodiment, an isolated nucleic acid molecule of the invention is at least 15 nucleotides in length and hybridizes under stringent conditions to the nucleic acid molecule comprising the nucleotide sequence of SEQ ID NO:1. In other embodiments, the nucleic acid is at least 30, 50, 100, 250 or 500 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. A preferred, non-limiting example of stringent hybridization conditions are hybridization in 6× sodium chloride/sodium citrate (SSC) at about 45° C., followed by one or more washes in 0.2× SSC, 0.1% SDS at 50–65° C. Preferably, an isolated nucleic acid molecule of the invention that hybridizes under stringent conditions to the sequence of SEQ ID NO:1 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural human flh2882.

In addition to naturally-occurring allelic variants of the flh2882 nucleic acid sequence that may exist in the population, the skilled artisan will further appreciate that changes can be introduced by mutation into the nucleotide sequence of SEQ ID NO:1, thereby leading to changes in the amino acid sequence of the encoded flh2882 protein, without altering the functional ability of the flh2882 protein. For example, nucleotide substitutions leading to amino acid substitutions at "non-essential" amino acid residues can be made in the sequence of SEQ ID NO:1. A "non-essential" amino acid residue is a residue that can be altered from the wild-type sequence of an flh2882 protein (e.g., the sequence of SEQ ID NO:2) without altering the activity of flh2882, whereas an "essential" amino acid residue is required for flh2882 protein activity. For example, conserved amino acid residues, e.g., aspartates, prolines, threonines, and tyrosines, in the transmembrane domains of the flh2882 protein are most likely important for binding to ligand and are thus essential residues of the flh2882 protein. Other amino acid residues, however, (e.g., those that are not conserved or only semi-conserved in the transmembrane domain) may not be essential for activity and thus are likely to be amenable to alteration without altering flh2882 protein activity.

Accordingly, another aspect of the invention pertains to nucleic acid molecules encoding flh2882 proteins that contain changes in amino acid residues that are not essential for flh2882 activity. Such flh2882 proteins differ in amino acid sequence from SEQ ID NO:2 yet retain at least one of the flh2882 activities described herein. In one embodiment, the isolated nucleic acid molecule comprises a nucleotide sequence encoding a protein, wherein the protein comprises an amino acid sequence at least about 30–35%, preferably at least about 40–45%, more preferably at least about 50–55%, even more preferably at least about 60–65%, yet more preferably at least about 70–75%, still more preferably at least about 80–85%, and most preferably at least about 90–95% or more homologous to the amino acid sequence of SEQ ID NO:2.

An isolated nucleic acid molecule encoding an flh2882 protein homologous to the protein of SEQ ID NO:2 can be created by introducing one or more nucleotide substitutions, additions or deletions into the nucleotide sequence of SEQ ID NO:1, such that one or more amino acid substitutions, additions or deletions are introduced into the encoded protein. Mutations can be introduced into SEQ ID NO:1 by standard techniques, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in flh2882 is preferably replaced with another amino acid residue from the same side chain family. Alternatively, in another embodiment, mutations can be introduced randomly along all or part of an flh2882 coding sequence, such as by saturation mutagenesis, and the resultant mutants can be screened for an flh2882 activity described herein to identify mutants that retain flh2882 activity. Following mutagenesis of SEQ ID NO:1, the encoded protein can be expressed recombinantly (e.g., as described in Examples 3 and 4) and the activity of the protein can be determined using, for example, assays described herein.

In addition to the nucleic acid molecules encoding flh2882 proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire flh2882 coding strand, or to only a fragment thereof. In one embodiment, an antisense nucleic acid molecule is antisense to a "coding region" of the coding strand of a nucleotide sequence encoding an flh2882 protein.

The term "coding region" refers to the region of the nucleotide sequence comprising codons which are translated into amino acid residues, e.g., the entire coding region of SEQ ID NO:1 comprises nucleotides 184 to 1194 (shown separately as SEQ ID NO:3). In another embodiment, the antisense nucleic acid molecule is antisense to a "noncoding region" of the coding strand of a nucleotide sequence encoding an flh2882 protein. The term "noncoding region" refers to 5' and 3' sequences which flank the coding region that are not translated into amino acids (i.e., also referred to as 5' and 3' untranslated regions).

Given the coding strand sequence encoding the flh2882 protein disclosed herein (e.g., SEQ ID NO:1), antisense nucleic acids of the invention can be designed according to the rules of Watson and Crick base pairing. The antisense nucleic acid molecule can be complementary to the entire coding region of flh2882 mRNA, but more preferably is an oligonucleotide which is antisense to only a fragment of the coding or noncoding region of flh2882 mRNA. For example, the antisense oligonucleotide can be complementary to the region surrounding the translation start site of flh2882 mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding an flh2882 protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of an antisense nucleic acid molecule of the invention includes direct injection at a tissue site. Alternatively, an antisense nucleic acid molecule can be modified to target selected cells and then administered systemically. For example, for systemic administration, an antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585–591)) can be used to catalytically cleave flh2882 mRNA transcripts to thereby inhibit translation of flh2882 mRNA. A ribozyme having specificity for an flh2882-encoding nucleic acid can be designed based upon the nucleotide sequence of an flh2882 cDNA disclosed herein (i.e., SEQ ID NO:1). For example, a derivative of a Tetrahymena L-19 IVS RNA can be constructed in which the nucleotide sequence of the active site is complementary to the nucleotide sequence to be cleaved in an flh2882-encoding mRNA. See, e.g., Cech et al. U.S. Pat. No. 4,987,071 and Cech et al. U.S. Pat. No. 5,116,742. Alternatively, flh2882 mRNA can be used to select a catalytic RNA having a specific ribonuclease activity from a pool of RNA molecules. See, e.g., Bartel, D. and Szostak, J. W. (1993) *Science* 261:1411–1418.

Alternatively, flh2882 gene expression can be inhibited by targeting nucleotide sequences complementary to the regulatory region of the flh2882 gene (e.g., the flh2882 gene promoter and/or enhancers) to form triple helical structures that prevent transcription of the flh2882 gene in target cells. See generally, Helene, C. (1991) *Anticancer Drug Des.* 6(6):569–84; Helene, C. et al. (1992) *Ann. N.Y. Acad. Sci.* 660:27–36; and Maher, L. J. (1992) *Bioassays* 14(12):807–15.

IV. Recombinant Expression Vectors and Host Cells

Another aspect of the invention pertains to vectors, preferably expression vectors, containing a nucleic acid encoding an flh2882 protein (or a fragment thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., flh2882 proteins, altered forms of flh2882 proteins, fusion proteins, and the like).

The recombinant expression vectors of the invention can be designed for expression of an flh2882 protein in prokaryotic or eukaryotic cells. For example, an flh2882 protein can be expressed in bacterial cells such as *E. coli*, insect cells (e.g., using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the flh2882 gene is cloned into a pGEX expression vector to create a vector encoding a fusion protein comprising, from the N-terminus to the C-terminus, GST-thrombin cleavage site-flh2882 protein. The fusion protein can be purified by affinity chromatography using glutathione-agarose resin. Recombinant flh2882 protein unfused to GST can be recovered by cleavage of the fusion protein with thrombin.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gnl). This viral polymerase is supplied by host strains BL21(DE3) or HMS174 (DE3) from a resident λ prophage harboring a T7 gnl gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

In another embodiment, the flh2882 gene expression vector is a yeast expression vector. Examples of vectors for expression in yeast *S. cerivisae* include pYepSec1 (Baldari, et al., (1987) *Embo J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, an flh2882 gene can be expressed in insect cells using, for example, baculovirus expression vectors. Baculovirus vectors available for expression of proteins in cultured insect cells (e.g., Sf9 cells) include the pAc series (Smith et al. (1983) *Mol. Cell Biol.* 3:2156–2165) and the pVL series (Lucklow and Summers (1989) *Virology* 170:31–39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *PNAS* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule encoding an flh2882 protein cloned into the expression vector in an antisense orientation. That is, the DNA molecule is operatively linked to a regulatory sequence in a manner which allows for expression (by transcription of the DNA molecule) of an RNA molecule which is antisense to flh2882 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics,* Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, flh2882 protein can be expressed in bacterial cells such as *E. coli,* insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual 2nd, ed., Cold Spring Harbor Laboratory,* Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding the flh2882 protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) flh2882 protein. Accordingly, the invention further provides methods for producing flh2882 protein using the host cells of the invention. In one embodiment, the method comprises culturing the host cell of invention (into which a recombinant expression vector encoding an flh2882 protein has been introduced) in a suitable medium until the flh2882 protein is produced. In another embodiment, the method further comprises isolating the flh2882 protein from the medium or the host cell.

The host cells of the invention can also be used to produce non-human transgenic animals. The non-human transgenic animals can be used in screening assays designed to identify agents or compounds, e.g., drugs, pharmaceuticals, etc., which are capable of ameliorating detrimental symptoms of selected disorders such as nervous system disorders, e.g., psychiatric disorders or disorders affecting circadian rhythms and the sleep-wake cycle. For example, in one embodiment, a host cell of the invention is a fertilized oocyte or an embryonic stem cell into which flh2882 protein-coding sequences have been introduced. Such host cells can then be used to create non-human transgenic animals in which exogenous flh2882 gene sequences have been introduced into their genome or homologous recombinant animals in which endogenous flh2882 gene sequences have been altered. Such animals are useful for studying the function and/or activity of an flh2882 protein and for identifying and/or evaluating modulators of flh2882 protein activity. As used herein, a "transgenic animal" is a non-human animal, preferably a mammal, more preferably a rodent such as a rat or mouse, in which one or more of the cells of the animal include a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous flh2882 gene has been altered by homologous recombination between the endogenous gene and an exogenous DNA molecule introduced into a cell of the animal, e.g., an embryonic cell of the animal, prior to development of the animal.

A transgenic animal of the invention can be created by introducing flh2882 protein encoding nucleic acid into the male pronuclei of a fertilized oocyte, e.g., by microinjection, retroviral infection, and allowing the oocyte to develop in a pseudopregnant female foster animal. The human flh2882 cDNA sequence of SEQ ID NO:1 can be introduced as a transgene into the genome of a non-human animal. Moreover, a non-human homologue of the human flh2882 gene, such as a mouse flh2882 gene, can be isolated based on hybridization to the human flh2882 cDNA (described further above) and used as a transgene. Intronic sequences and polyadenylation signals can also be included in the transgene to increase the efficiency of expression of the transgene. A tissue-specific regulatory sequence(s) can be operably linked to the flh2882 transgene to direct expression of an flh2882 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the flh2882 transgene in its genome and/or expression of flh2882 mRNA in tissues or cells of the animals. A transgenic founder animal can then be used to breed additional animals carrying the transgene. Moreover, transgenic animals carrying a transgene encoding an flh2882 protein can further be bred to other transgenic animals carrying other transgenes.

To create a homologous recombinant animal, a vector is prepared which contains at least a fragment of an flh2882 gene into which a deletion, addition or substitution has been introduced to thereby alter, e.g., functionally disrupt, the flh2882 gene. The flh2882 gene can be a human gene (e.g., from a human genomic clone isolated from a human genomic library screened with the cDNA of SEQ ID NO:1), but more preferably is a non-human homologue of a human flh2882 gene. For example, a mouse flh2882 gene can be isolated from a mouse genomic DNA library using the flh2882 cDNA of SEQ ID NO:1 as a probe. The mouse flh2882 gene then can be used to construct a homologous recombination vector suitable for altering an endogenous flh2882 gene in the mouse genome. In a preferred embodiment, the vector is designed such that, upon homologous recombination, the endogenous flh2882 gene is functionally disrupted (i.e., no longer encodes a functional protein; also referred to as a "knock out" vector). Alternatively, the vector can be designed such that, upon homologous recombination, the endogenous flh2882 gene is mutated or otherwise altered but still encodes functional protein (e.g., the upstream regulatory region can be altered to thereby alter the expression of the endogenous flh2882 protein). In the homologous recombination vector, the altered fragment of the flh2882 gene is flanked at its 5' and 3' ends by additional nucleic acid of the flh2882 gene to allow for homologous recombination to occur between the exogenous flh2882 gene carried by the vector and an endogenous flh2882 gene in an embryonic stem cell. The additional flanking flh2882 nucleic acid is of sufficient length for successful homologous recombination with the endogenous gene. Typically, several kilobases of flanking DNA (both at the 5' and 3' ends) are included in the vector (see for example, Thomas, K. R. and Capecchi, M. R. (1987) *Cell* 51:503 for a description of homologous recombination vectors). The vector is introduced into an embryonic stem cell line (e.g., by electroporation) and cells in which the introduced flh2882 gene has homologously recombined with the endogenous flh2882 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos. WO 90/11354; WO 91/01140; WO 92/0968; and WO 93/04169.

In another embodiment, transgenic non-human animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *PNAS* 89:6232–6236. Another example of a recombinase system is the FLP recombinase system of *Saccharomyces cerevisiae* (O'Gorman et al. (1991) *Science* 251:1351–1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810–813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring borne of this female foster animal will be a clone of the animal from which the cell, e.g., the somatic cell, is isolated.

V. Uses and Methods of the Invention

The nucleic acid molecules, proteins, protein homologues, modulators, and antibodies described herein can be used in one or more of the following methods: a) drug screening assays; b) diagnostic assays particularly in disease identification, allelic screening and pharmocogenetic testing; c) methods of treatment; d) pharmacogenomics; and e) monitoring of effects during clinical trials. An flh2882 protein of the invention can be used as a drug target for developing agents to modulate the activity of the flh2882 protein (a GPCR). The isolated nucleic acid molecules of the invention can be used to express flh2882 protein (e.g., via a recombinant expression vector in a host cell or in gene therapy applications), to detect flh2882 mRNA (e.g., in a biological sample) or a naturally occurring or recombinantly generated genetic mutation in an flh2882 gene, and to modulate flh2882 protein activity, as described further below. In addition, the flh2882 proteins can be used to screen drugs or compounds which modulate flh2882 protein activity. Moreover, the anti-flh2882 antibodies of the invention can be used to detect and isolate an flh2882 protein, particularly fragments of an flh2882 protein present in a biological sample, and to modulate flh2882 protein activity.

a. Drug Screening Assays

The invention provides methods for identifying compounds or agents that can be used to treat disorders characterized by (or associated with) aberrant or abnormal flh2882 nucleic acid expression and/or flh2882 protein activity. These methods are also referred to herein as drug screening assays and typically include the step of screening a candidate/test compound or agent to identify compounds that are an agonist or antagonist of an flh2882 protein, and specifically for the ability to interact with (e.g., bind to) an flh2882 protein, to modulate the interaction of an flh2882 protein and a target molecule, and/or to modulate flh2882 nucleic acid expression and/or flh2882 protein activity. Candidate/test compounds or agents which have one or more of these abilities can be used as drugs to treat disorders characterized by aberrant or abnormal flh2882 nucleic acid expression and/or flh2882 protein activity. Candidate/test compounds include, for example, 1) peptides such as soluble peptides, including Ig-tailed fusion peptides and members of random peptide libraries (see, e.g., Lam, K. S. et al. (1991) *Nature* 354:82–84; Houghten, R. et al. (1991) *Nature* 354:84–86) and combinatorial chemistry-derived molecular libraries made of D- and/or L- configuration amino acids; 2) phosphopeptides (e.g., members of random and partially degenerate, directed phosphopeptide libraries, see, e.g., Songyang, Z. et al. (1993) *Cell* 72:767–778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

In one embodiment, the invention provides assays for screening candidate/test compounds which interact with (e.g., bind to) an flh2882 protein. Typically, the assays are recombinant cell based or cell-free assays which include the steps of combining a cell expressing an flh2882 protein or a bioactive fragment thereof, or an isolated flh2882 protein, and a candidate/test compound, e.g., under conditions which allow for interaction of (e.g., binding of) the candidate/test compound to the flh2882 protein or fragment thereof to form a complex, and detecting the formation of a complex, in which the ability of the candidate compound to interact with (e.g., bind to) the flh2882 protein or fragment thereof is indicated by the presence of the candidate compound in the complex. Formation of complexes between the flh2882 protein and the candidate compound can be detected using competition binding assays, and can be quantitated, for example, using standard immunoassays.

In another embodiment, the invention provides screening assays to identify candidate/test compounds which modulate (e.g., stimulate or inhibit) the interaction (and most likely flh2882 protein activity as well) between an flh2882 protein and a molecule (target molecule) with which the flh2882 protein normally interacts. Examples of such target molecules include proteins in the same signaling path as the flh2882 protein, e.g., proteins which may function upstream (including both stimulators and inhibitors of activity) or downstream of the flh2882 protein in, for example, a cognitive function signaling pathway or in a pathway involving flh2882 protein activity, e.g., a G protein or other interactor involved in cAMP or phosphatidylinositol turnover, and/or adenylate cyclase or phospholipase C activation. Typically, the assays are recombinant cell based assays which include the steps of combining a cell expressing an flh2882 protein, or a bioactive fragment thereof, an flh2882 protein target molecule (e.g., an flh2882 ligand) and a candidate/test compound, e.g., under conditions wherein but for the presence of the candidate compound, the flh2882 protein or biologically active fragment thereof interacts with (e.g., binds to) the target molecule, and detecting the formation of a complex which includes the flh2882 protein and the target molecule or detecting the interaction/reaction of the flh2882 protein and the target molecule. Detection of complex formation can include direct quantitation of the complex by, for example, measuring inductive effects of the flh2882 protein. A statistically significant change, such as a decrease, in the interaction of the flh2882 protein and target molecule (e.g., in the formation of a complex between the flh2882 protein and the target molecule) in the presence of a candidate compound (relative to what is detected in the absence of the candidate compound) is indicative of a modulation (e.g., stimulation or inhibition) of the interaction between the flh2882 protein and the target molecule. Modulation of the formation of complexes between the flh2882 protein and the target molecule can be quantitated using, for example, an immunoassay.

To perform cell free drug screening assays, it is desirable to immobilize either the flh2882 protein or its target molecule to facilitate separation of complexes from uncomplexed forms of one or both of the proteins, as well as to accommodate automation of the assay. Interaction (e.g., binding of) of the flh2882 protein to a target molecule, in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows the protein to be bound to a matrix. For example, glutathione-S-transferase/flh2882 fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of flh2882-binding protein found in the bead fraction quantitated from the gel using standard electrophoretic techniques.

Other techniques for immobilizing proteins on matrices can also be used in the drug screening assays of the invention. For example, either the flh2882 protein or its target molecule can be immobilized utilizing conjugation of biotin and streptavidin. Biotinylated flh2882 protein molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with an flh2882 protein but which do not interfere with binding of the protein to its target molecule can be derivatized to the wells of the plate, and flh2882 protein trapped in the wells by antibody conjugation. As described above, preparations of an flh2882-binding protein and a candidate compound are incubated in the flh2882 protein-presenting wells of the plate, and the amount of complex trapped in the well can be quantitated. Methods for detecting such complexes, in addition to those described above for the GST-immobilized complexes, include immunodetection of complexes using antibodies reactive with the flh2882 protein target molecule, or which are reactive with flh2882 protein and compete with the target molecule; as well as enzyme-linked assays which rely on detecting an enzymatic activity associated with the target molecule.

In yet another embodiment, the invention provides a method for identifying a compound (e.g., a screening assay) capable of use in the treatment of a disorder characterized by (or associated with) aberrant or abnormal flh2882 nucleic acid expression or flh2882 protein activity. This method typically includes the step of assaying the ability of the compound or agent to modulate the expression of the flh2882 nucleic acid or the activity of the flh2882 protein thereby identifying a compound for treating a disorder characterized by aberrant or abnormal flh2882 nucleic acid expression or flh2882 protein activity. Methods for assaying the ability of the compound or agent to modulate the expression of the flh2882 nucleic acid or activity of the flh2882 protein are typically cell-based assays. For example, cells which are sensitive to ligands which transduce signals via a pathway involving an flh2882 protein can be induced to overexpress an flh2882 protein in the presence and absence of a candidate compound. Candidate compounds which produce a statistically significant change in flh2882 protein-dependent responses (either stimulation or inhibition) can be identified. In one embodiment, expression of the flh2882 nucleic acid or activity of an flh2882 protein is modulated in cells and the effects of candidate compounds on the readout of interest (such as cAMP or phosphatidylinositol turnover) are measured. For example, the expression of genes which are up- or down-regulated in response to an flh2882 protein-dependent signal cascade can be assayed. In preferred embodiments, the regulatory regions of such genes, e.g., the 5' flanking promoter and enhancer regions, are operably linked to a detectable marker (such as luciferase) which encodes a gene product that can be readily detected. Phosphorylation of an flh2882 protein or flh2882 protein target molecules can also be measured, for example, by immunoblotting.

Alternatively, modulators of flh2882 gene expression (e.g., compounds which can be used to treat a disorder characterized by aberrant or abnormal flh2882 nucleic acid expression or flh2882 protein activity) can be identified in a method wherein a cell is contacted with a candidate compound and the expression of flh2882 mRNA or protein in the cell is determined. The level of expression of flh2882 mRNA or protein in the presence of the candidate compound is compared to the level of expression of flh2882 mRNA or protein in the absence of the candidate compound. The candidate compound can then be identified as a modulator of flh2882 nucleic acid expression based on this comparison and be used to treat a disorder characterized by aberrant flh2882 nucleic acid expression. For example, when expression of flh2882 mRNA or protein is greater (statistically significantly greater) in the presence of the candidate compound than in its absence, the candidate compound is identified as a stimulator of flh2882 nucleic acid expression. Alternatively, when flh2882 nucleic acid expression is less (statistically significantly less) in the presence of the candidate compound than in its absence, the candidate compound is identified as an inhibitor of flh2882 nucleic acid expression. The level of flh2882 nucleic acid expression in the cells can be determined by methods described herein for detecting flh2882 mRNA or protein.

In yet another aspect of the invention, the flh2882 proteins, or fragments thereof, can be used as "bait proteins" in a two-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO 94/10300), to identify other proteins, which bind to or interact with the flh2882 protein ("flh2882-binding proteins" or "flh2882-bp") and modulate flh2882 protein activity. Such flh2882-binding proteins are also likely to be involved in the propagation of signals by the flh2882 proteins as, for example, upstream or downstream elements of the flh2882 protein pathway.

The two-hybrid system is based on the modular nature of most transcription factors, which consist of separable DNA-binding and activation domains. Bartel, P. et al. "Using the Two-Hybrid System to Detect Protein-Protein Interactions" in Cellular Interactions in Development: A Practical Approach, Hartley, D. A. ed. (Oxford University Press, Oxford, 1993) pp. 153–179. Briefly, the assay utilizes two different DNA constructs. In one construct, the gene that encode an flh2882 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an flh2882-protein dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the flh2882 protein.

Modulators of flh2882 protein activity and/or flh2882 nucleic acid expression identified according to these drug screening assays can be used to treat, for example, nervous system disorders. These methods of treatment include the steps of administering the modulators of flh2882 protein activity and/or nucleic acid expression, e.g., in a pharmaceutical composition as described in subsection IV above, to a subject in need of such treatment, e.g., a subject with a disorder described herein.

b. Diagnostic Assays

The invention further provides a method for detecting the presence of an flh2882 protein or flh2882 nucleic acid molecule, or fragment thereof, in a biological sample. The method involves contacting the biological sample with a compound or an agent capable of detecting flh2882 protein or mRNA such that the presence of flh2882 protein/encoding nucleic acid molecule is detected in the biological sample. A preferred agent for detecting flh2882 mRNA is a labeled or labelable nucleic acid probe capable of hybridizing to flh2882 mRNA. The nucleic acid probe can be, for example, the full-length flh2882 cDNA of SEQ ID NO:1, or a fragment thereof, such as an oligonucleotide of at least 15, 30, 50, 100, 250 or 500 nucleotides in length and sufficient to specifically hybridize under stringent conditions to flh2882 mRNA. A preferred agent for detecting flh2882 protein is a labeled or labelable antibody capable of binding to flh2882 protein. Antibodies can be polyclonal, or more preferably, monoclonal. An intact antibody, or a fragment thereof (e.g., Fab or F(ab')$_2$) can be used. The term "labeled or labelable", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect flh2882 mRNA or protein in a biological sample in vitro as well as in vivo. For example, in vitro techniques for detection of flh2882 mRNA include Northern hybridizations and in situ hybridizations. In vitro techniques for detection of flh2882 protein include enzyme linked immunosorbent assays (ELISAs), Western blots, immunoprecipitations and immunofluorescence. Alternatively, flh2882 protein can be detected in vivo in a subject by introducing into the subject a labeled anti-flh2882 antibody. For example, the antibody can be labeled with a radioactive marker whose presence and location in a subject can be detected by standard imaging techniques. Particularly useful are methods which detect the allelic variant of an flh2882 protein expressed in a subject and methods which detect fragments of an flh2882 protein in a sample.

The invention also encompasses kits for detecting the presence of an flh2882 protein in a biological sample. For example, the kit can comprise reagents such as a labeled or labelable compound or agent capable of detecting flh2882 protein or mRNA in a biological sample; means for determining the amount of flh2882 protein in the sample; and means for comparing the amount of flh2882 protein in the sample with a standard. The compound or agent can be packaged in a suitable container. The kit can further comprise instructions for using the kit to detect flh2882 mRNA or protein.

The methods of the invention can also be used to detect naturally occurring genetic mutations in an flh2882 gene, thereby determining if a subject with the mutated gene is at risk for a disorder characterized by aberrant or abnormal flh2882 nucleic acid expression or flh2882 protein activity as described herein. In preferred embodiments, the methods include detecting, in a sample of cells from the subject, the presence or absence of a genetic mutation characterized by at least one of an alteration affecting the integrity of a gene encoding an flh2882 protein, or the misexpression of the flh2882 gene. For example, such genetic mutations can be detected by ascertaining the existence of at least one of 1) a deletion of one or more nucleotides from an flh2882 gene; 2) an addition of one or more nucleotides to an flh2882 gene; 3) a substitution of one or more nucleotides of an flh2882 gene, 4) a chromosomal rearrangement of an flh2882 gene; 5) an alteration in the level of a messenger RNA transcript of an flh2882 gene, 6) aberrant modification of an flh2882 gene, such as of the methylation pattern of the genomic DNA, 7) the presence of a non-wild type splicing pattern of a messenger RNA transcript of an flh2882 gene, 8) a non-wild type level of an flh2882-protein, 9) allelic loss of an flh2882 gene, and 10) inappropriate post-translational modification of an flh2882-protein. As described herein, there are a large number of assay techniques known in the art that can be used for detecting mutations in an flh2882 gene.

In certain embodiments, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *PNAS* 91:360–364), the latter of which can be particularly useful for detecting point mutations in the flh2882-gene (see Abravaya et al. (1995) *Nucleic Acids Res.* 23:675–682). This method can include the steps of collecting a sample of cells from a patient, isolating nucleic acid (e.g., genomic, mRNA or both) from the cells of the sample, contacting the nucleic acid sample with one or more primers which specifically hybridize to an flh2882 gene under conditions such that hybridization and amplification of the flh2882-gene (if present) occurs, and detecting the presence or absence of an amplification product, or detecting the size of the amplification product and comparing the length to a control sample.

In an alternative embodiment, mutations in an flh2882 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In yet another embodiment, any of a variety of sequencing reactions known in the art can be used to directly sequence the flh2882 gene and detect mutations by comparing the sequence of the sample flh2882 gene with the corresponding wild-type (control) sequence. Examples of sequencing reactions include those based on techniques developed by Maxim and Gilbert ((1977) *PNAS* 74:560) or Sanger ((1977) *PNAS* 74:5463). A variety of automated sequencing procedures can be utilized when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the flh2882 gene include methods in which protection from cleavage agents is used to detect mismatched bases in RNA/RNA or RNA/DNA duplexes (Myers et al. (1985) *Science* 230:1242); Cotton et al. (1988) *PNAS* 85:4397; Saleeba et al. (1992) *Meth. Enzymol.* 217:286–295), electrophoretic mobility of mutant and wild type nucleic acid is compared (Orita et al. (1989) *PNAS* 86:2766; Cotton (1993) *Mutat. Res.* 285:125–144; and Hayashi (1992) *Genet. Anal. Tech. Appl.* 9:73–79), and movement of mutant or wild-type fragments in polyacrylamide gels containing a gradient of denaturant is assayed using denaturing gradient gel electrophoresis (Myers et al (1985) *Nature* 313:495). Examples of other techniques for detecting point mutations include, selective oligonucleotide hybridization, selective amplification, and selective primer extension.

c. Methods of Treatment

Another aspect of the invention pertains to methods for treating a subject, e.g., a human, having a disease or disorder characterized by (or associated with) aberrant or abnormal flh2882 nucleic acid expression and/or flh2882 protein activity. These methods include the step of administering an flh2882 protein/gene modulator (agonist or antagonist) to the subject such that treatment occurs. The language "aberrant or abnormal flh2882 protein expression" refers to expression of a non-wild-type flh2882 protein or a non-wild-type level of expression of an flh2882 protein. Aberrant or abnormal flh2882 protein activity refers to a non-wild-type flh2882 protein activity or a non-wild-type level of flh2882 protein activity. As the flh2882 protein is involved in a pathway involving signaling within cells, aberrant or abnormal flh2882 protein activity or expression interferes with the normal regulation of functions mediated by flh2882 protein signaling, and in particular brain cells.

The terms "treating" or "treatment", as used herein, refer to reduction or alleviation of at least one adverse effect or symptom of a disorder or disease, e.g., a disorder or disease characterized by or associated with abnormal or aberrant flh2882 protein activity or flh2882 nucleic acid expression.

As used herein, an flh2882 protein/gene modulator is a molecule which can modulate flh2882 nucleic acid expression and/or flh2882 protein activity. For example, an flh2882 gene or protein modulator can modulate, e.g., upregulate (activate/agonize) or downregulate (suppress/antagonize), flh2882 nucleic acid expression. In another example, an flh2882 protein/gene modulator can modulate (e.g., stimulate/agonize or inhibit/antagonize) flh2882 protein activity. If it is desirable to treat a disorder or disease characterized by (or associated with) aberrant or abnormal (non-wild-type) flh2882 nucleic acid expression and/or flh2882 protein activity by inhibiting flh2882 nucleic acid expression, an flh2882 modulator can be an antisense molecule, e.g., a ribozyme, as described herein. Examples of antisense molecules which can be used to inhibit flh2882 nucleic acid expression include antisense molecules which are complementary to a fragment of the 5' untranslated region of SEQ ID NO:1 which also includes the start codon and antisense molecules which are complementary to a fragment of the 3' untranslated region of SEQ ID NO:1. An example of an antisense molecule which is complementary to a fragment of the 5' untranslated region of SEQ ID NO:1 and which also includes the start codon is a nucleic acid molecule which includes nucleotides which are complementary to nucleotides 171 to 186 of SEQ ID NO:1. This antisense molecule has the following nucleotide sequence: 5° CGGGGCGCGCACCATG 3' (SEQ ID NO:11). An additional example of an antisense molecule which is complementary to a fragment of the 5' untranslated region of SEQ ID NO:1 and which also includes the start codon is a nucleic acid molecule which includes nucleotides which are complementary to nucleotides 180 to 196 of SEQ ID NO:1. This antisense molecule has the following nucleotide sequence: 5' CACCATGAACTCGTGGG 3' (SEQ ID NO:12). An example of an antisense molecule which is complementary to a fragment of the 3' untranslated region of SEQ ID NO:1 is a nucleic acid molecule which includes nucleotides which are complementary to nucleotides 1195 to 1210 of SEQ ID NO:1. This antisense molecule has the following sequence: 5' TGAAGGACCGCGCTCC 3' (SEQ ID NO:13). An additional example of an antisense molecule which is complementary to a fragment of the 3' untranslated region of SEQ ID NO:1 is a nucleic acid molecule which includes nucleotides which are complementary to nucleotides 1189 to 1204 of SEQ ID NO:1. This antisense molecule has the following sequence: 5' TCTGAGTGAAGGACCG 3' (SEQ ID NO:14).

An flh2882 modulator that inhibits flh2882 nucleic acid expression can also be a small molecule or other drug, e.g., a small molecule or drug identified using the screening assays described herein, which inhibits flh2882 nucleic acid expression. If it is desirable to treat a disease or disorder characterized by (or associated with) aberrant or abnormal (non-wild-type) flh2882 nucleic acid expression and/or flh2882 protein activity by stimulating flh2882 nucleic acid expression, an flh2882 modulator can be, for example, a nucleic acid molecule encoding an flh2882 protein (e.g., a nucleic acid molecule comprising a nucleotide sequence homologous to the nucleotide sequence of SEQ ID NO:1) or a small molecule or other drug, e.g., a small molecule (peptide) or drug identified using the screening assays described herein, which stimulates flh2882 nucleic acid expression.

Alternatively, if it is desirable to treat a disease or disorder characterized by (or associated with) aberrant or abnormal (non-wild-type) flh2882 nucleic acid expression and/or flh2882 protein activity by inhibiting flh2882 protein activity, an flh2882 modulator can be an anti-flh2882 antibody or a small molecule or other drug, e.g., a small molecule or drug identified using the screening assays described herein, which inhibits flh2882 protein activity. If it is desirable to treat a disease or disorder characterized by (or associated with) aberrant or abnormal (non-wild-type) flh2882 nucleic acid expression and/or flh2882 protein activity by stimulating flh2882 protein activity, an flh2882 modulator can be an active flh2882 protein or fragment thereof (e.g., an flh2882 protein or fragment thereof having an amino acid sequence which is homologous to the amino acid sequence of SEQ ID NO:2 or a fragment thereof) or a small molecule or other drug, e.g., a small molecule or drug identified using the screening assays described herein, which stimulates flh2882 protein activity.

Other aspects of the invention pertain to methods for modulating an flh2882 protein mediated cell activity. These methods include contacting the cell with an agent (or a composition which includes an effective amount of an agent) which modulates flh2882 protein activity or flh2882 nucleic acid expression such that an flh2882 protein mediated cell activity is altered relative to normal levels (for example, cAMP or phosphatidylinositol metabolism). As used herein, "an flh2882 protein mediated cell activity" refers to a normal or abnormal activity or function of a cell. Examples of flh2882 protein mediated cell activities include phosphatidylinositol turnover, production or secretion of molecules, such as proteins, contraction, proliferation, migration, differentiation, and cell survival. In a preferred embodiment, the cell is neural cell of the brain, e.g., a hippocampal cell. The term "altered" as used herein refers to a change, e.g., an increase or decrease, of a cell associated activity particularly cAMP or phosphatidylinositol turnover, and adenylate cyclase or phospholipase C activation. In one embodiment, the agent stimulates flh2882 protein activity or flh2882 nucleic acid expression. In another embodiment, the agent inhibits flh2882 protein activity or flh2882 nucleic acid expression. These modulatory methods can be performed in vitro (e.g., by culturing the cell with the agent) or, alternatively, in vivo (e.g., by administering the agent to a subject). In a preferred embodiment, the modulatory methods are performed in vivo, i.e., the cell is present within a subject, e.g., a mammal, e.g., a human, and the subject has a disorder or disease characterized by or associated with abnormal or aberrant flh2882 protein activity or flh2882 nucleic acid expression.

A nucleic acid molecule, a protein, an flh2882 modulator, a compound etc. used in the methods of treatment can be incorporated into an appropriate pharmaceutical composition described below and administered to the subject through a route which allows the molecule, protein, modulator, or compound etc. to perform its intended function.

d. Pharmacogenomics

Test/candidate compounds, or modulators which have a stimulatory or inhibitory effect on flh2882 protein activity (e.g., flh2882 gene expression) as identified by a screening assay described herein can be administered to individuals to treat (prophylactically or therapeutically) disorders (e.g., CNS disorders) associated with aberrant flh2882 protein activity. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmacogenomics of the individual permit the selection of effective compounds (e.g., drugs) for prophylactic or therapeutic treatments based on a consideration of the individual's genotype. Such pharmacogenomics can further be used to determine appropriate dosages and therapeutic regimens. Accordingly, the activity of flh2882 protein, expression of flh2882 nucleic acid, or mutation content of flh2882 genes in an individual can be determined to thereby select appropriate compound(s) for therapeutic or prophylactic treatment of the individual.

Pharmacogenomics deal with clinically significant hereditary variations in the response to drugs due to altered drug disposition and abnormal action in affected persons. See, e.g., Eichelbaum, M. (1996) *Clin. Exp. Pharmacol. Physiol.* 23(10–11):983–985 and Linder, M. W. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of flh2882 protein, expression of flh2882 nucleic acid, or mutation content of flh2882 genes in an individual can be determined to thereby select appropriate agent(s) for therapeutic or prophylactic treatment of a subject. In addition, pharmacogenetic studies can be used to apply genotyping of polymorphic alleles encoding drug-metabolizing enzymes to the identification of a subject's drug responsiveness phenotype. This knowledge, when applied to dosing or drug selection, can avoid adverse reactions or therapeutic failure and thus enhance therapeutic or prophylactic efficiency when treating a subject with an flh2882 modulator, such as a modulator identified by one of the exemplary screening assays described herein.

e. Monitoring of Effects during Clinical Trials

Monitoring the influence of compounds (e.g., drugs) on the expression or activity of flh2882 protein/gene can be applied not only in basic drug screening, but also in clinical trials. For example, the effectiveness of an agent determined by a screening assay, as described herein, to increase flh2882 gene expression, protein levels, or up-regulate flh2882 activity, can be monitored in clinical trials of subjects exhibiting decreased flh2882 gene expression, protein levels, or down-regulated flh2882 protein activity. Alternatively, the effectiveness of an agent, determined by a screening assay, to decrease flh2882 gene expression, protein levels, or down-regulate flh2882 protein activity, can be monitored in clinical trials of subjects exhibiting increased flh2882 gene expression, protein levels, or upregulated flh2882 protein activity. In such clinical trials, the expression or activity of an flh2882 protein and, preferably, other genes which have been implicated in, for example, a nervous system related disorder can be used as a "read out" or markers of the ligand responsiveness of a particular cell.

For example, and not by way of limitation, genes, including an flh2882 gene, which are modulated in cells by treatment with a compound (e.g., drug or small molecule) which modulates flh2882 protein/gene activity (e.g., identified in a screening assay as described herein) can be identified. Thus, to study the effect of compounds on CNS disorders, for example, in a clinical trial, cells can be isolated and RNA prepared and analyzed for the levels of expression of an flh2882 gene and other genes implicated in the disorder. The levels of gene expression (i.e., a gene expression pattern) can be quantified by Northern blot analysis or RT-PCR, as described herein, or alternatively by measuring the amount of protein produced, by one of the methods described herein, or by measuring the levels of activity of an flh2882 protein or other genes. In this way, the gene expression pattern can serve as an marker, indicative of the physiological response of the cells to the compound. Accordingly, this response state may be determined before, and at various points during, treatment of the individual with the compound.

In a preferred embodiment, the present invention provides a method for monitoring the effectiveness of treatment of a subject with a compound (e.g., an agonist, antagonist, peptidomimetic, protein, peptide, nucleic acid, small molecule, or other drug candidate identified by the screening assays described herein) comprising the steps of (i) obtaining a pre-administration sample from a subject prior to administration of the compound; (ii) detecting the level of expression of an flh2882 protein, mRNA, or genomic DNA in the preadministration sample; (iii) obtaining one or more post-administration samples from the subject; (iv) detecting the level of expression or activity of the flh2882 protein, mRNA, or genomic DNA in the post-administration samples; (v) comparing the level of expression or activity of the flh2882 protein, mRNA, or genomic DNA in the pre-administration sample with the flh2882 protein, mRNA, or genomic DNA in the post administration sample or samples; and (vi) altering the administration of the compound to the subject accordingly. For example, increased administration of the compound may be desirable to increase the expression or activity of an flh2882 protein/gene to higher levels than detected, i.e., to increase the effectiveness of the agent. Alternatively, decreased administration of the agent may be desirable to decrease expression or activity of flh2882 to lower levels than detected, i.e. to decrease the effectiveness of the compound.

VI. Pharmaceutical Compositions

The flh2882 nucleic acid molecules, flh2882 proteins (particularly fragments of flh2882), modulators of an flh2882 protein, and anti-flh2882 antibodies (also referred to herein as "active compounds") of the invention can be incorporated into pharmaceutical compositions suitable for administration to a subject, e.g., a human. Such compositions typically comprise the nucleic acid molecule, protein, modulator, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an flh2882 protein or anti-flh2882 antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) PNAS 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g. retroviral vectors, the pharmaceutical preparation can include one or more cells which produce the gene delivery system.

The pharmaceutical compositions can be included in a container, pack, or dispenser together with instructions for administration.

VII. Uses of Partial flh2882 Sequences

Fragments or fragments of the cDNA sequences identified herein (and the corresponding complete gene sequences) can be used in numerous ways as polynucleotide reagents. For example, these sequences can be used to: (a) map their respective genes on a chromosome; and, thus, locate gene regions associated with genetic disease; (b) identify an individual from a minute biological sample (tissue typing); and (c) aid in forensic identification of a biological sample. These applications are described in the subsections below.

a. Chromosome Mapping

Once the sequence (or a fragment of the sequence) of a gene has been isolated, this sequence can be used to map the location of the gene on a chromosome. This process is called chromosome mapping. Accordingly, fragments of an flh2882 nucleic acid sequences can be used to map the location of the flh2882 gene, respectively, on a chromosome. The mapping of the flh2882 sequence to chromosomes is an important first step in correlating these sequence with genes associated with disease.

Briefly, the flh2882 gene can be mapped to a chromosome by preparing PCR primers (preferably 15–25 bp in length) from the flh2882 gene sequence. Computer analysis of the flh2882 gene sequence can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the flh2882 gene sequence will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919–924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the flh2882 gene sequence to design oligonucleotide primers, sublocalization can be achieved with panels of fragments from specific chromosomes. Other mapping strategies which can similarly be used to map an flh2882 gene sequence to its chromosome include in situ hybridization (described in Fan, Y. et al. (1990) *PNAS*, 87:6223–27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York, 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data (such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, for example, Egeland, J. et al. (1987) *Nature* 325:783–787.

Moreover, differences in the DNA sequences between individuals affected and unaffected with a disease associated with the flh2882 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

b. Tissue Typing

The flh2882 gene sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected fragments of an individual's genome. Thus, the flh2882 sequences described herein can be used to prepare two PCR primers from the 5' and 3' ends of the sequences. These primers can then be used to amplify an individual's DNA and subsequently sequence it.

Panels of corresponding DNA sequences from individuals prepared in this manner can provide unique individual identifications, as each individual will have a unique set of such DNA sequences due to allelic differences. The sequences of the present invention can be used to obtain such identification sequences from individuals and from tissue. The flh2882 gene sequences of the invention uniquely represent fragments of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequence of SEQ ID NO:1, can comfortably provide positive individual identification with a panel of perhaps 10 to 1,000 primers which each yield a noncoding amplified sequence of 100 bases. If a predicted coding sequence, such as that in SEQ ID NO:3, is used, a more appropriate number of primers for positive individual identification would be 500–2,000.

If a panel of reagents from the flh2882 gene sequences described herein is used to generate a unique identification database for an individual, those same reagents can later be used to identify tissue from that individual. Using the unique identification database, positive identification of the individual, living or dead, can be made from extremely small tissue samples.

c. Use of Partial flh2882 Gene Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As described above, actual base sequence information can be used for identification as an accurate alternative to patterns formed by restriction enzyme generated fragments. Sequences targeted to the noncoding region of SEQ ID NO:1 are particularly appropriate for this use as greater numbers of polymorphisms occur in the noncoding regions, making it easier to differentiate individuals using this technique. Examples of polynucleotide reagents include the flh2882 sequences or fragments thereof, e.g., fragments derived from the noncoding region of SEQ ID NO:1, having a length of at least 20 bases, preferably at least 30 bases.

The flh2882 sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such flh2882 probes can be used to identify tissue by species and/or by organ type.

In a similar fashion, these reagents, e.g., flh2882 primers or probes can be used to screen tissue culture for contamination (i.e., screen for the presence of a mixture of different types of cells in a culture).

This invention is further illustrated by the following examples which should not be construed as limiting. The contents of all references, patent applications, patents, and published patent applications cited throughout this application are hereby incorporated by reference.

EXAMPLES

Example 1

Identification of Human flh2882 cDNA

In this example, the human flh2882 nucleic acid molecule was identified by screening appropriate cDNA libraries. A non-annotated EST was first identified and used to screen a human fetal cDNA library. Several positive clones were identified, sequenced, and the sequences were assembled. BLAST analysis of nucleic acid databases in the public domain showed homologies only to the 3' untranslated region of the flh2882 nucleic acid molecule and the original EST (GenBank™ Accession No. T09060).

Example 2

Tissue Expression of the flh2882 Gene

Northern Analysis using RNA from Human Tissue

Human brain multiple tissue northern (MTN) blots, human MTN I, II, and III blots (Clontech, Palo Alto, Calif.), containing 2 µg of poly A+RNA per lane were probed with human flh2882-specific primers (probes). The filters were prehybridized in 10 ml of Express Hyb hybridization solution (Clontech, Palo Alto, Calif.) at 68° C. for 1 hour, after which 100 ng of $^{32}$P labeled probe was added. The probe was generated using the Stratagene Prime-It kit, Catalog No. 300392 (Clontech, Palo Alto, Calif.). Hybridization was allowed to proceed at 68° C. for approximately 2 hours. The filters were washed in a 0.05% SDS/2×SSC solution for 15 minutes at room temperature and then twice with a 0.1% SDS/0.1×SSC solution for 20 minutes at 50° C. and then exposed to autoradiography film overnight at −80° C. with one screen. The human tissues tested included: heart, brain (regions of the brain tested included cerebellum, cerebral cortex, medulla, spinal cord, occipital pole, frontal lobe, temporal lobe, putamen, amygdala, caudate nucleus, hippocampus, corpus callosum, substantia nigra, subthalamic nucleus and thalamus), placenta, lung, liver, skeletal muscle, kidney, pancreas, spleen, thymus, prostate, testis, uterus, small intestine, colon (mucosal lining), and peripheral blood leukocyte.

There was a strong hybridization to human whole brain, and the substantia nigra indicating that the approximately 2.6 kb flh2882 gene transcript is expressed in these tissues.

Example 3

Expression of Recombinant flh2882 Protein in Bacterial Cells

In this example, flh2882 is expressed as a recombinant glutathione-S-transferase (GST) fusion protein in E. coli and the fusion protein is isolated and characterized. Specifically, flh2882 is fused to GST and this fusion protein is expressed in E. coli, e.g., strain PEB199. As the human protein is predicted to be approximately 38.7 kDa, and GST is predicted to be 26 kDa, the fusion protein is predicted to be approximately 64.7 kDa, in molecular weight. Expression of the GST-flh2882 fusion protein in PEB199 is induced with IPTG. The recombinant fusion protein is purified from crude bacterial lysates of the induced PEB199 strain by affinity chromatography on glutathione beads. Using polyacrylamide gel electrophoretic analysis of the protein purified from the bacterial lysates, the molecular weight of the resultant fusion protein is determined.

Example 4

Expression of Recombinant flh2882 Protein in COS Cells

To express the flh2882 gene in COS cells, the pcDNA/Amp vector by Invitrogen Corporation (San Diego, Calif.) is used. This vector contains an SV40 origin of replication, an ampicillin resistance gene, an E. coli replication origin, a CMV promoter followed by a polylinker region, and an SV40 intron and polyadenylation site. A DNA fragment encoding the entire flh2882 protein and a HA tag (Wilson et al. (1984) Cell 37:767) fused in-frame to its 3' end of the fragment is cloned into the polylinker region of the vector, thereby placing the expression of the recombinant protein under the control of the CMV promoter.

To construct the plasmid, the flh2882 DNA sequence is amplified by PCR using two primers. The 5' primer contains the restriction site of interest followed by approximately twenty nucleotides of the flh2882 coding sequence starting from the initiation codon; the 3' end sequence contains complementary sequences to the other restriction site of interest, a translation stop codon, the HA tag and the last 20 nucleotides of the flh2882 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the flh2882 gene is inserted in the correct orientation. The ligation mixture is transformed into E coli cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the flh2882-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. Molecular Cloning: A Laboratory Manual. 2nd, ed., Cold Spring Harbor Laboratory, Cold Spring Harbor Laboratory Press, Cold Spring Harbor, N.Y., 1989. The expression of the flh2882 protein is detected by radiolabelling ($^{35}$S-methionine or $^{35}$S-cysteine available from NEN, Boston, Mass., can be used) and immunoprecipitation (Harlow, E. and Lane, D. Antibodies: A Laboratory Manual, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1%

NP-40, 0.1% SDS, 0.5% DOC, 50 mM Tris, pH 7.5). Both the cell lysate and the culture media are precipitated with an HA specific monoclonal antibody. Precipitated proteins are then analyzed by SDS-PAGE.

Alternatively, DNA containing the flh2882 coding sequence is cloned directly into the polylinker of the pCDNA/Amp vector using the appropriate restriction sites. The resulting plasmid is transfected into COS cells in the manner described above, and the expression of the flh2882 protein is detected by radiolabelling and immunoprecipitation using an flh2882 specific monoclonal antibody

Example 5

Characterization of the Human flh2882 Protein

In this example, the amino acid sequence of the human flh2882 protein was compared to amino acid sequences of known proteins and various motifs were identified.

The human flh2882 protein, the amino acid sequence of which is shown in FIG. 3 (SEQ ID NO:2), is a novel protein which includes 337 amino acid residues. Hydrophobicity analysis indicated that the human flh2882 protein contains seven transmembrane domains between amino acid residues 11–28 (SEQ ID NO:4), 43–62 (SEQ ID NO:5), 80–102 (SEQ ID NO:6), 121–146 (SEQ ID NO:7), 169–190 (SEQ ID NO:8), 247–265 (SEQ ID NO:9), and 280–300 (SEQ ID NO:10). The nucleotide sequence of the human flh2882 was used as a database query using the BLASTN program (BLASTN1.3MP, Altschul et al. (1990) *J. Mol. Biol.* 215:403). The closest hit was to the mouse 5HT5$_B$ receptor (GenBank™ Accession No. P31387). The highest similarity is 24/77 amino acid identities.

Equivalents

Those skilled in the art will recognize, or be able to ascertain using no more than routine experimentation, many equivalents to the specific embodiments of the invention described herein. Such equivalents are intended to be encompassed by the following claims.

---

What is claimed is:

1. An isolated nucleic acid molecule comprising a nucleotide sequence selected from the group consisting of:
   a) a nucleotide sequence which encodes a protein comprising the amino acid sequence of SEQ ID NO:2;
   b) the nucleotide sequence of SEQ ID NO:1;
   c) the nucleotide sequence of SEQ ID NO:3;
   d) a nucleotide sequence which is complementary to the nucleotide sequence of SEQ ID NO:1; and
   e) a nucleotide sequence which is complementary to the nucleotide sequence of SEQ ID NO:3.

2. A vector comprising the nucleic acid molecule of claim 1.

3. An isolated host cell transfected or transformed with the nucleic acid molecule of claim 1.

4. A method of expressing a polypeptide comprising the amino acid sequence of SEQ ID NO:2, said method comprising the step of culturing the isolated host cell of claim 3 under conditions in which the nucleic acid molecule is expressed, thereby expressing the polypeptide.

5. A method of producing a polypeptide comprising the amino acid sequence of SEQ ID NO:2, said method comprising the step of culturing the isolated host cell of claim 3 under conditions in which the nucleic acid molecule is expressed and isolating said polypeptide from the culture medium.

6. An isolated nucleic acid molecule comprising a nucleotide sequence which encodes a naturally occurring allelic variant of a protein consisting of the amino acid sequence of SEQ ID NO:2, wherein said nucleic acid molecule hybridizes to a complement of a nucleic acid molecule consisting of SEQ ID NO:3 at 6×SSC at 45° C., followed by one or more washes in 0.2×SSC, 0.1% SDS at 50–65° C.

7. A vector comprising the nucleic acid molecule of claim 6.

8. An isolated host cell transfected or transformed with the nucleic acid molecule of claim 1.

9. A method of expressing a polypeptide comprising a naturally occurring allelic variant of a protein consisting of the amino acid sequence of SEQ ID NO:2, said method comprising the step of culturing the isolated host cell of claim 8 under conditions in which the nucleic acid molecule is expressed, thereby expressing the polypeptide.

10. A method of producing a polypeptide comprising a naturally occurring allelic variant of a protein consisting of the amino acid sequence of SEQ ID NO:2, said method comprising the step of culturing the isolated host cell of claim 8 under conditions in which the nucleic acid molecule is expressed and isolating said polypeptide from the culture medium.

11. An isolated nucleic acid molecule consisting of a nucleotide sequence which encodes a protein consisting of the amino acid sequence of SEQ ID NO:2.

12. A vector comprising the nucleic acid molecule of claim 11.

13. An isolated host cell transfected or transformed with the nucleic acid molecule of claim 11.

14. An isolated nucleic acid molecule consisting of a nucleotide sequence which encodes a naturally occurring allelic variant of a protein consisting of the amino acid sequence of SEQ ID NO:2, wherein said nucleic acid molecule hybridizes to a complement of a nucleic acid molecule consisting of SEQ ID NO:3 at 6×SSC at 45° C., followed by one or more washes in 0.2×SSC, 0.1% SDS at 50–65° C.

15. A vector comprising the nucleic acid molecule of claim 14.

16. An isolated host cell transfected or transformed with the nucleic acid molecule of claim 14.

* * * * *

UNITED STATES PATENT AND TRADEMARK OFFICE
CERTIFICATE OF CORRECTION

PATENT NO. : 5,945,307
DATED : August 31, 1999
INVENTOR(S) : M. Alexandra Glucksmann et al.

It is certified that error appears in the above-identified patent and that said Letters Patent is hereby corrected as shown below:

At column 56, line 12, please delete "claim 1" and insert - - claim 6 - -.

Signed and Sealed this

Third Day of October, 2000

*Attest:*

*Attesting Officer*

Q. TODD DICKINSON

*Director of Patents and Trademarks*